US010952976B2

(12) United States Patent
Galer et al.

(10) Patent No.: US 10,952,976 B2
(45) Date of Patent: *Mar. 23, 2021

(54) COMPOSITIONS AND METHODS FOR TREATING RESPIRATORY DEPRESSION WITH FENFLURAMINE

(71) Applicant: ZOGENIX INTERNATIONAL LIMITED, Berkshire (GB)

(72) Inventors: Bradley S. Galer, West Chester, PA (US); Carl L. Faingold, Springfield, FL (US); Parthena Martin, Emeryville, CA (US)

(73) Assignee: ZOGENIX INTERNATIONAL LIMITED, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/692,968

(22) Filed: Nov. 22, 2019

(65) Prior Publication Data
US 2020/0330406 A1    Oct. 22, 2020

Related U.S. Application Data

(62) Division of application No. 16/432,468, filed on Jun. 5, 2019, now Pat. No. 10,517,841.

(60) Provisional application No. 62/685,200, filed on Jun. 14, 2018.

(51) Int. Cl.
*A61K 31/40* (2006.01)
*A61K 31/137* (2006.01)
*A61K 31/435* (2006.01)
*A61K 31/445* (2006.01)
*A61P 11/00* (2006.01)
*A61P 25/08* (2006.01)

(52) U.S. Cl.
CPC ............ *A61K 31/137* (2013.01); *A61P 25/08* (2018.01)

(58) Field of Classification Search
CPC .... A61K 31/40; A61K 31/137; A61K 31/435; A61K 31/445; A61P 11/00
USPC .............. 514/231.5, 294, 327, 418, 422, 649
See application file for complete search history.

(56) References Cited

U.S. PATENT DOCUMENTS

| 4,452,815 | A | 6/1984 | Wurtman |
| 5,834,477 | A | 11/1998 | Mioduszewski |
| 5,985,880 | A | 11/1999 | Chang |
| 6,599,901 | B1 | 7/2003 | Flohr |
| 9,125,900 | B2 | 9/2015 | Meyer |
| 9,549,909 | B2 | 1/2017 | Ceulemens |
| 9,603,814 | B2 | 3/2017 | Ceulemens |
| 9,603,815 | B2 | 3/2017 | Ceulemens |
| 9,610,260 | B2 | 4/2017 | Ceulemens |
| 10,517,841 | B1 * | 12/2019 | Galer ............. A61K 31/5375 |
| 2003/0118654 | A1 | 5/2003 | Santos et al. |
| 2005/0182103 | A1 | 8/2005 | Finke et al. |
| 2006/0121066 | A1 | 6/2006 | Jaeger et al. |
| 2006/0270611 | A1 | 11/2006 | Dries et al. |
| 2008/0261962 | A1 | 10/2008 | Greer |
| 2010/0298181 | A1 | 11/2010 | Hanada et al. |
| 2011/0092535 | A1 | 4/2011 | Barnes et al. |
| 2011/0212171 | A1 | 9/2011 | Venkatesh et al. |
| 2011/0230473 | A1 | 9/2011 | Gordon et al. |
| 2012/0115958 | A1 | 5/2012 | Mariotti et al. |
| 2012/0157392 | A1 | 6/2012 | Martin et al. |
| 2012/0270848 | A1 | 10/2012 | Mannion |
| 2013/0296398 | A1 | 11/2013 | Whalley |
| 2014/0030343 | A1 | 1/2014 | Lamson |
| 2014/0162942 | A1 | 6/2014 | Ghosal |
| 2014/0329908 | A1 | 11/2014 | Ceulemens et al. |
| 2014/0343162 | A1 | 11/2014 | Ceulemens et al. |
| 2015/0080377 | A1 | 3/2015 | Dhanoa |
| 2015/0291597 | A1 | 10/2015 | Mannion |
| 2015/0359755 | A1 | 12/2015 | Guy et al. |
| 2016/0136114 | A1 | 5/2016 | Ceulemens et al. |
| 2016/0228454 | A1 | 8/2016 | Zhang et al. |
| 2017/0020885 | A1 | 1/2017 | Hsu |
| 2017/0056344 | A1 | 3/2017 | Farr et al. |
| 2017/0071949 | A1 | 3/2017 | De Witte et al. |
| 2017/0151214 | A1 | 6/2017 | Ceulemens et al. |
| 2017/0174613 | A1 | 6/2017 | Londesbrough et al. |

(Continued)

FOREIGN PATENT DOCUMENTS

JP    H05-310564 A    11/1993
WO    WO 2005/004865    1/2005

(Continued)

OTHER PUBLICATIONS

Anandam, R., Affiliations Indian Journal of Pediatrics (Jan. 1, 2000) 67 (1 Suppl):S88-91 (Abstract Only).
Anonymous, "Determination That PONDIMIN (Fenfluramine Hydrochloride) Tablets, 20 Milligrams and 60 Milligrams, and Ponderex (Fenfluramine Hydrochloride) Capsules, 20 Milligrams Were Withdrawn From Sale for Reasons of Safety or Effectiveness", Federal Register, (Sep. 29, 2015).

(Continued)

*Primary Examiner* — Raymond J Henley, III
(74) *Attorney, Agent, or Firm* — Karl Bozicevic; Bozicevic Field & Francis LLP

(57) ABSTRACT

5-HT receptor agonists are useful in the treatment of a variety of diseases. Provided herein are methods of treating and/or reducing the occurrence of respiratory depression caused by an opioid in a human patient or patient population using a 5-HT receptor agonist, such as, for example, a 5-HT4 agonist (e.g., fenfluramine). Methods of stimulating one or more 5-HT$_4$ receptors in the brain of a patient undergoing treatment with an opioid, wherein the patient is at risk of respiratory depression, by administering a 5-HT4 agonist (e.g., fenfluramine) to a subject in need thereof are provided. Pharmaceutical compositions for use in practicing the subject methods are also provided.

13 Claims, 12 Drawing Sheets

(56) References Cited

U.S. PATENT DOCUMENTS

| | | |
|---|---|---|
| 2017/0348303 A1 | 12/2017 | Bosse |
| 2018/0028499 A1 | 2/2018 | Baraban et al. |
| 2018/0092864 A1 | 4/2018 | Martin et al. |
| 2018/0141953 A1 | 5/2018 | Dax |
| 2018/0148403 A1 | 5/2018 | Londesbrough et al. |
| 2018/0215701 A1 | 8/2018 | Carroll et al. |

FOREIGN PATENT DOCUMENTS

| | | |
|---|---|---|
| WO | WO 2008/025148 | 3/2008 |
| WO | WO 2010/020585 | 2/2010 |
| WO | WO 2014/177676 | 11/2014 |
| WO | WO 2015/026849 | 2/2015 |
| WO | WO 2015/066344 | 5/2015 |
| WO | WO 2015/193668 | 12/2015 |
| WO | WO 2016/138138 | 9/2016 |
| WO | WO 2017/035267 | 3/2017 |
| WO | WO 2018/037306 | 3/2018 |
| WO | WO 2018/060732 | 4/2018 |
| WO | WO 2018/206924 | 11/2018 |

OTHER PUBLICATIONS

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Anonymous "Selective Serotonin reuptake Inhibitor—Wikipedia" Internet https://en.wikipedia.org/wiki/Selective_serotonin_reuptake_inhibitor (Feb. 1, 2020 (retrived on Feb. 4, 2020)).

Arzimanoglou, "Dravet syndrome: From electroclinical characteristics to molecular biology" Epilepsia, 50(Suppl. 8):3-9 (2009).

Boel and Casaer, " Add-on Therapy of Fenfluramine in Intractable Self-Induced Epilepsy" Neuropaediatrics 1996, 27(4):171-173.

F Brenot et al., "Primary Pulmonary Hypertension and Fenfluramine Use.", Heart, vol. 70, No. 6, Dec. 1, 1993 (Dec. 1, 1993), pp. 537-541.

Brunklaus et al., "Prognostic, clinical and demographic features in SCN1A mutation-positive Dravet syndrome" Brain, 2012, p. 1-8.

Brunklaus et al., "Dravet syndrome—From epileptic encephalopathy to channelopathy" Epilepsia (May 16, 2014) 55(7):979-984.

Buchanan, Gordon F. et al., Serotonin neurones have anticonvulsant effects and reduce seizure-induced mortality, The Journal of Physiology, 2014, vol. 592, Issue 19, p. 4395-4410.

Carvalho et al., "d-Amphetamine Interaction with Glutathione in Freshly Isolated Rat Hepatocytes" Chemical Research in Toxicology (Jan. 1996) 9(6):1031-1036.

Casaer et al., "Fenfluramine as a Potential Antiepileptic Drug" Epilepsia, 43(2), 205-206, 2002.

C. B. Catarino et al. "Dravet Syndrome as epileptic encephalopathy: Evidence from long-term course and neuropathology", Brain, vol. 134, No. 10 (Jun. 29, 2011) pp. 2982-3010.

Ceulemans et al., "Poster presented at the 69th Annual Meeting of the American Epilepsy Society" (Dec. 2015) Philadelphia.

Ceulemans et al., "Successful use of fenfluramine as an add-on treatment for Dravet syndrome" Epilepsia, 53(7), 2012, 1131-1139.

Ceulemans, "Overall management of patients with Dravet syndrome" Developmental Medicine & Child Neurology, 2011, 53, 19-23.

Ceulemans B. et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).

Ceulemans B., "Successful Use of Fenfluramine as Add-On Treatment in Dravet Syndrome" Epilepsia, 52(Suppl. 6):4-22 (2011).

Ceulemans et al., "Five-year extended follow-up status of 10 patients with Dravet syndrome treated with fenfluramine" Epilepsia (May 20, 2016) 57(7):e129-e134.

Chiron et. al., "The pharmacologic treatment of Dravet syndrome" Epilepsia (2011) 52(Suppl 2):72-75.

Clemens B., "Dopamine agonist treatment of self-induced pattern-sensitive epilepsy. A case Report" Epilepsy Res. 2. 1988, p. 340-343.

Curzon et al., "Appetite suppression by commonly used drugs depends on 5-HT receptors but not on 5-HT availability" Tips (1997) 18:21-25.

Devinsky et al., "Trial of Cannabidiol for Drug-Resistant Seizures in the Dravet Syndrome" The New Engalnd Journal of Medicine (May 25, 2017) 376(21):2011-2020.

C. Doege et al., "Myoclonic-astatic epilepsy: Doose-Syndrum 2014: Doose syndrome 2014", Zeitschrift FR Epileptologie, (Mar. 20, 2014).

Doring et al. "Thirty Years of Orphan Drug Legislation and the Development of Drugs to Treat Rare Seizure Conditions: A Cross Sectional Analysis" PLOS One, pp. 1-15 (Aug. 24, 2016).

Dravet, Charlotte, "The core Dravet syndrome phenotype" Epilepsia, 52(Supp. 2):3-9 (2011).

Faingold et al., "Prevention of seizure-induced sudden death in a chronic SUDEP model by semichronic administration of a selective serotonin reuptake inhibitor" Epilepsy & Behavior (2011) 22:186-190.

Favale et al., "The anticonvulsant effect of citalopram as indirect evidence of serotonergic impairment in human epileptogenesis" Seizure (2003) 12:316-319.

Franco-Perez, Javier "The Selective Serotonin Reuptake Inhibitors: Antidepressants with Anticonvulsant Effects?" Ann Deoress Anxiety (2014) 1(5):1025 (2 pages).

Gastaut et al., "Compulsive respiratory sterotypies in children with autistic features: Polygraphic recording and treatment with fenfluramine" Journal of Autism and Developmental Disorders, (Sep. 1, 1987) 17(3):391-406.

K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 925-928.

Gharedaghi et al., "The role of different serotonin receptor subtypes in seizure susceptibility" Exp. Brain Res (2014) 232:347-367.

Gioia et al., "Confirmatory Factor Analysis of the Behavior Rating Inventory of Executive Function (BRIEF) in a Clinical Sample" Child Neuropsychology (2002) 8(4):249-57.

Habibi et al., "The Impact of Psychoactive Drugs on Seizures and Antiepileptic Drugs" Current Neurology and Neuroscience Reports (Jun. 17, 2016) 16(8):1-10.

Haritos et al., "Metabolism of dexfenfluramine in human liver microsomes and by recombinant enzymes: Role of CYP2D6 and 1A2" Pharmcogenetics (Oct. 1998) 8(5):423-432.

Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se. . .).

Hazai et al., "Reduction of toxic metabolite formation of acetaminophen" Biochemical and Biophysical Research Communications (Mar. 8, 2002) 291(4):1089-1094.

Hegadoren et al., "Interactions of iprindole with fenfluramine metabolism in rat brain and liver" Journal of Psychiatry & Neuroscience (Mar. 1991) pp. 5-11.

Inoue et al., "Stiripentol open study in Japanese patients with Dravet Syndrome" Epilepsia, 50(11):2362-2368 (2009).

Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.

Katholieke Universiteit Leuven, University Hospital Antwerp: "Interim results of a fenfluramine open-label extension study", European Patent Register (May 25, 2017).

Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.

Lagae et al. "A pilot, open-label study of the effectiveness and tolerability of low-dose ZX008 (fenfluramine HC1) in Lennox-Gastaut syndrome" Epilepsia (2018) 59: 1881-1888.

Leit, Silvana et al., Design and synthesis of tryptamine-based 5HT2C agonists for the treatment of certain CNS disorders, Divi-

(56) References Cited

OTHER PUBLICATIONS sion of Medicinal Chemistry Scientific Abstracts for the 240th National ACS Meeting and Exposition, Jul. 28, 2010, MEDI367.
LeJeune et al, "Psychometric Support for an Abbreviated Version of the Behavior Rating Inventory of Executive Function (BRIEF) Parent Form" Child Neuropsychology (2010 16:182-201.
Lopez-Meraz et al., "5-HT$_{1A}$ receptor agonist modify epileptic seizures in three experimental models in rats" Neuropharmacology (2005) 49:367-375.
Manzke et al., "5-HT4(a) receptors avert opiod-induced breathing depression without loss of analgesia" Science (Jul. 11, 2003) 301:226-229.
Martin, et al., "An Examination of the Mechanism of Action of Fenfluramine in Dravet Syndrome: A Look Beyond Serotonin" Presented as part of the Zogenix Scientific Exhibit During the 70$^{th}$ Annual Meeting of the American Epilepsy Society, Houston, Texas (Dec. 2-6, 2016).
Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.
Mudigoudar et al., "Emerging Antiepileptic Drugs for Severe Pediatric Epilepsies" Seminars in Pediatric Neurology (Jun. 2016) 23(2):167-179.
Mulley et al., "SCN1A Mutations and Epilepsy" Human Mutation (2005) 25:535-542.
Naithani et al., "The Conventional Antiepileptic Drug Use When Compared to a Combination Therapy Regime in a Teaching Hospital in India" International Journal of Pharma and Bio Sciences (2012) 3(1):B-191-B-197.
NCT02682927 (Sep. 3, 2016, 10 pages) Accessed from https://www.clinicaltrials.gov/ct2/history/NCT02682927?V=View#StudyPageTop on Mar. 18, 2019).
Nozulak et al., "(+)-cis-4,5,7a,8,9,10,11,11a-Octahydro-7H-10-methylindolo[1,7-bc][2,6]-naphthridine: A 5-HT$_{2C/2B}$ Receptor Antagonist with Low 5-HT$_{2A}$ Receptor Affinity" J. Med. Chem. (1995) 38:28-33.
O'Neill et al., "GR46611 potentiates 5-HT$_{1A}$ receptor-mediated locomotor activity in the guinea pig"European Journal of Pharmacology (1999) 370:85-92.
Pirincci et al., "The Effects of Fefluramine on Blood and Tissue Seratonin (5-Hydroxytryptamine) Levels in Rats" Turk J Vet Anim Sci (2005) 29:857-863.
Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.
Jake Remaly: "Fenfluramine Reduces Convulsive Seizure Frequency in Dravet Syndrome. Epilepsy Resource Center", Jan. 1, 2018 (Jan. 1, 2018).
Remington, "The Science and Practice of Pharmacy", Nineteenth Edition (1995), pp. 710-712.
Rho, Jong M. "Basic Science Behind the Catastrophic Epilepsies" Epilepsia (2004) 45(Suppl. 5):5-11.
Rothman et al., "Serotonergic drugs and valvular heart disease" Expert Opinion on Drug Safety (May 2009) 8(3):317-329.
Schoonjans, An-Sofie "Low-dose fenfluramine in the treatment of neurologic disorders: experience in Dravet syndrome" Therapeutic Advances in Neurological Disorders (Jan. 1, 2015) pp. 328-338.
Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.
An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.
Selmer et al., "SCN1A mutation screening in adult patients with Lenox-Gastaut syndrome features" Epilepsy & Behavior (Nov. 1, 2009) 16(3):555-57.
Sharma et al. Indian Journal of Pharmacology, 1996, 28(1), 1-10.
Sourbron et al., "Serotonergic Modulation as Effective Treatment for Dravet Syndrome in Zebrafish Mutant Model" ACS Chemical Neuroscience (Feb. 17, 2016) 7(5):588-598.
Sullivan et al. "Effext of ZX008 (fenfluramine HC1 oral solution) on total seizures in Dravet syndrome" Neurology: Official Journal of the American Academy of Neurology, 2018, 90(24):e2187-e2811.
Van Rijckevorsel, Kenou, "Treatment of Lennox-Gastaut syndrome: overview and recent findings" Neuropsychiatric Disease and Treatment, 4(6):1001-1019 (2008).
Vickers et al., "Oral Administration of the 5-HT2C receptor agonist, mCPP, reduces body weight gain in rats over 28 days as a result of maintained hypophagia" Psychopharmacology (May 2003), 167 (3): 274-280.
Viola et al., "The Behavior Rating Inventory of Executive Function (BRIEF) to Identify Pediatric Acute Lymphoblastic Leukemia (ALL) Survivors at Risk for Neurocognitive Impairment" Journal of Pediatric Hematology/Oncology (Apr. 1, 2017) 39(3):174-178.
Wallace et al., "Pharmacotherapy for Dravet Syndrome" Paediatr. Drugs, 18(3):197-208 (Jun. 2016).
Wirrell et al., "Stiripentol in Dravet syndrome: Results of a retrospective U.S. study" Epilepsia (2013) 54(9):1595-1604.
Wirrell et al., "Stiripentol in Dravet Syndrome: Is it Worth It?" Epilepsy Currents, 14(1):22-23 (Jan./Feb. 2014).
Wirrell et al., "Treatment of Dravet Syndrome" Can. J. Neurol. Sci., 43(Suppl. 3):S13-18 (Jun. 2016).
Wirrell et al., "Optimizing the Diagnosis and Management of Dravet Syndrome: Recommendations From a North American Consensus Panel" Pediatric Neurology (Mar. 2017) 68:18-34.
Wurtman et al., "Fenfluramine and other serotoninergic drugs depress food intake and carbohydrate consumption while sparing protein consumption" Current Medical Research and Opinion (1979) 6(1 Supp):28-33.
Yamaori et al., "Potent inhibition of human cytochrome P450 3A isoforms by cannabidiol: Role of phenolic hydroxyl groups in the resorcinol moiety" Life Sciences (2011) 88:730-736.
Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.
Zhang et al., *A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS)*. Presented at the 2016 American Conference for Pharmacokinetics.
Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts accepted for American Conference on Pharmacometrics 2016 (ACoP7).
Zhang et al., "Pharmacological Characterization of an Antisense Knockdown Zebrafish Model of Dravet Syndrome: Inhibition of Epileptic Seizures by the Serotonin Agonist Fenfluramine" PLOS One (May 12, 2015) 10(5)::16-17 (Abstract).
Zhuang et al. (2016), "PBPK modeling and simulation in drug research and development" in Acta Pharmaceutica Sinica B 2016;6(5):430-440.
Zogenix "Corporate Update Nasdaq: ZGNX" (Jun. 1, 2016) Retrieved from the Internet: URL:http://www.jefferies.com/CMSFiles/Jefferies.com.files/Conferences/060716/Presentations/Zogenix%20Inc.pdf [retrieved on Feb. 21, 2018].

\* cited by examiner

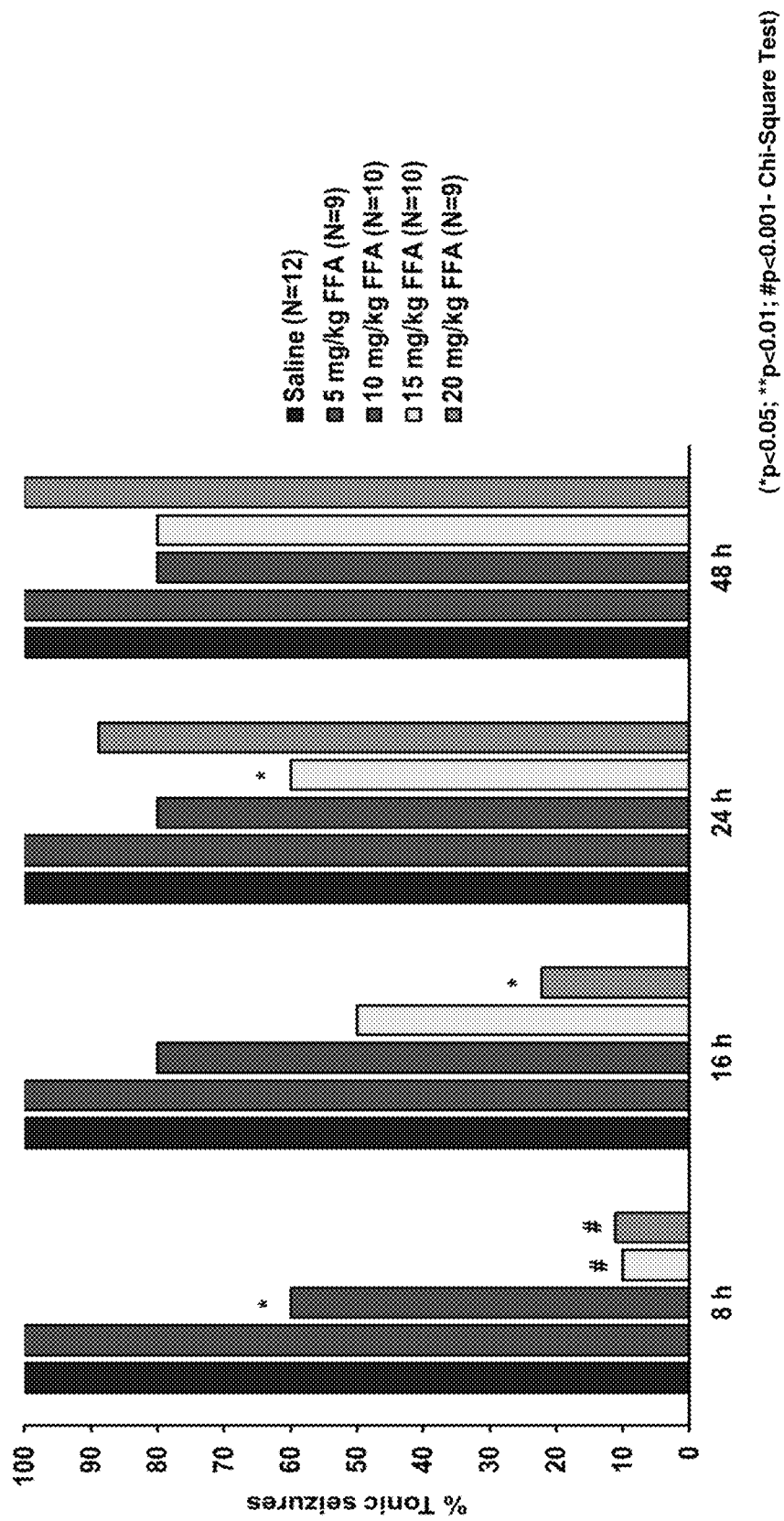

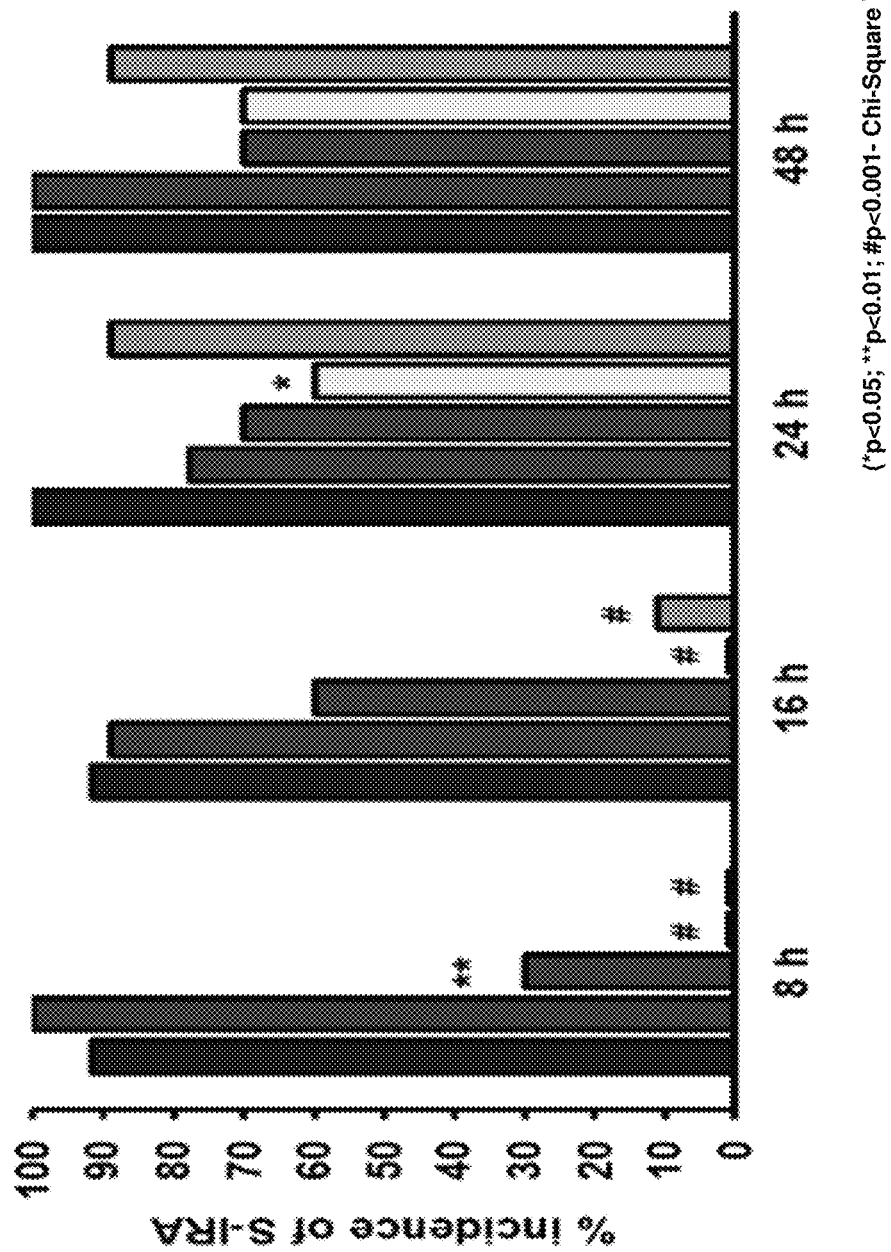

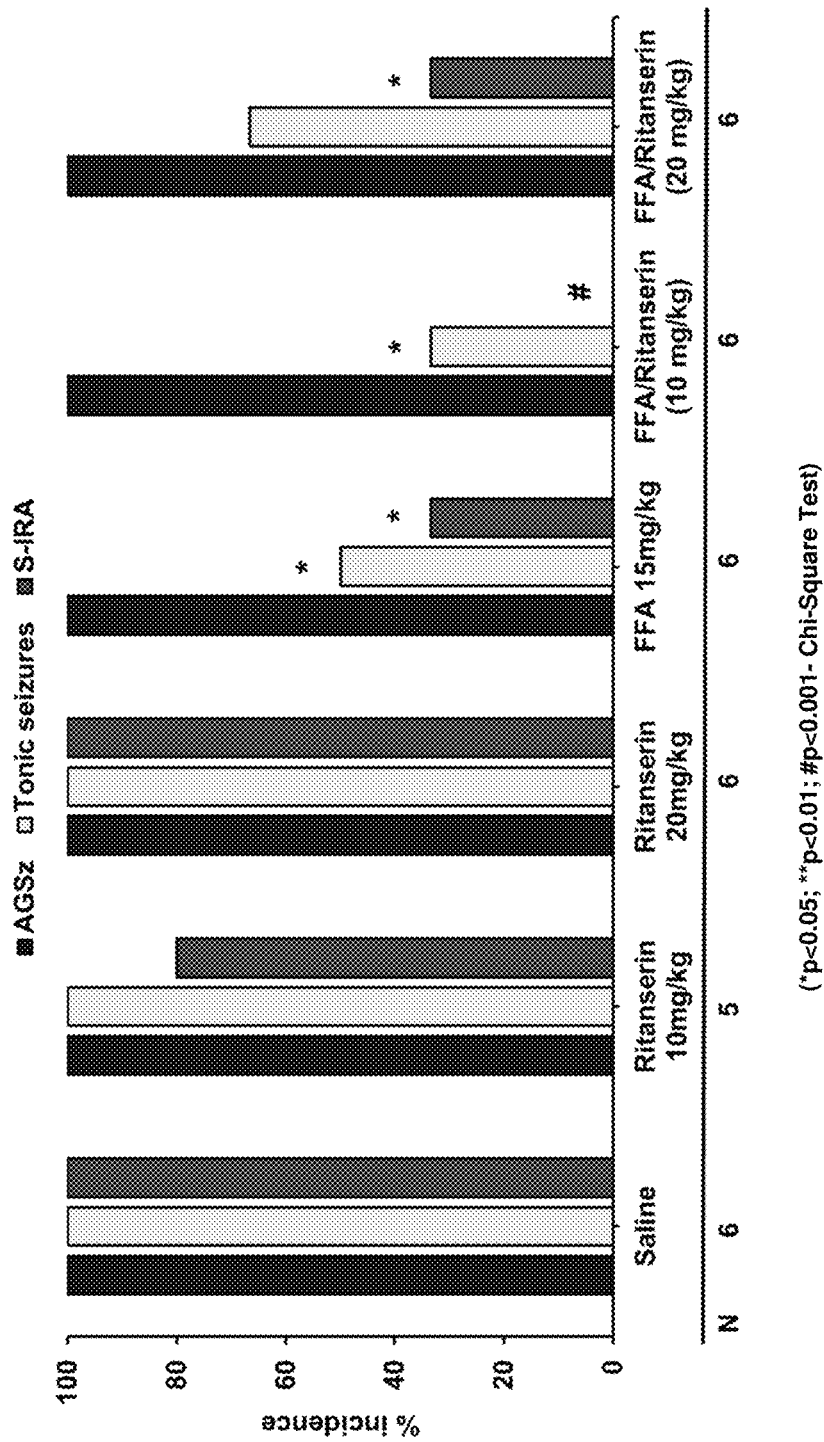

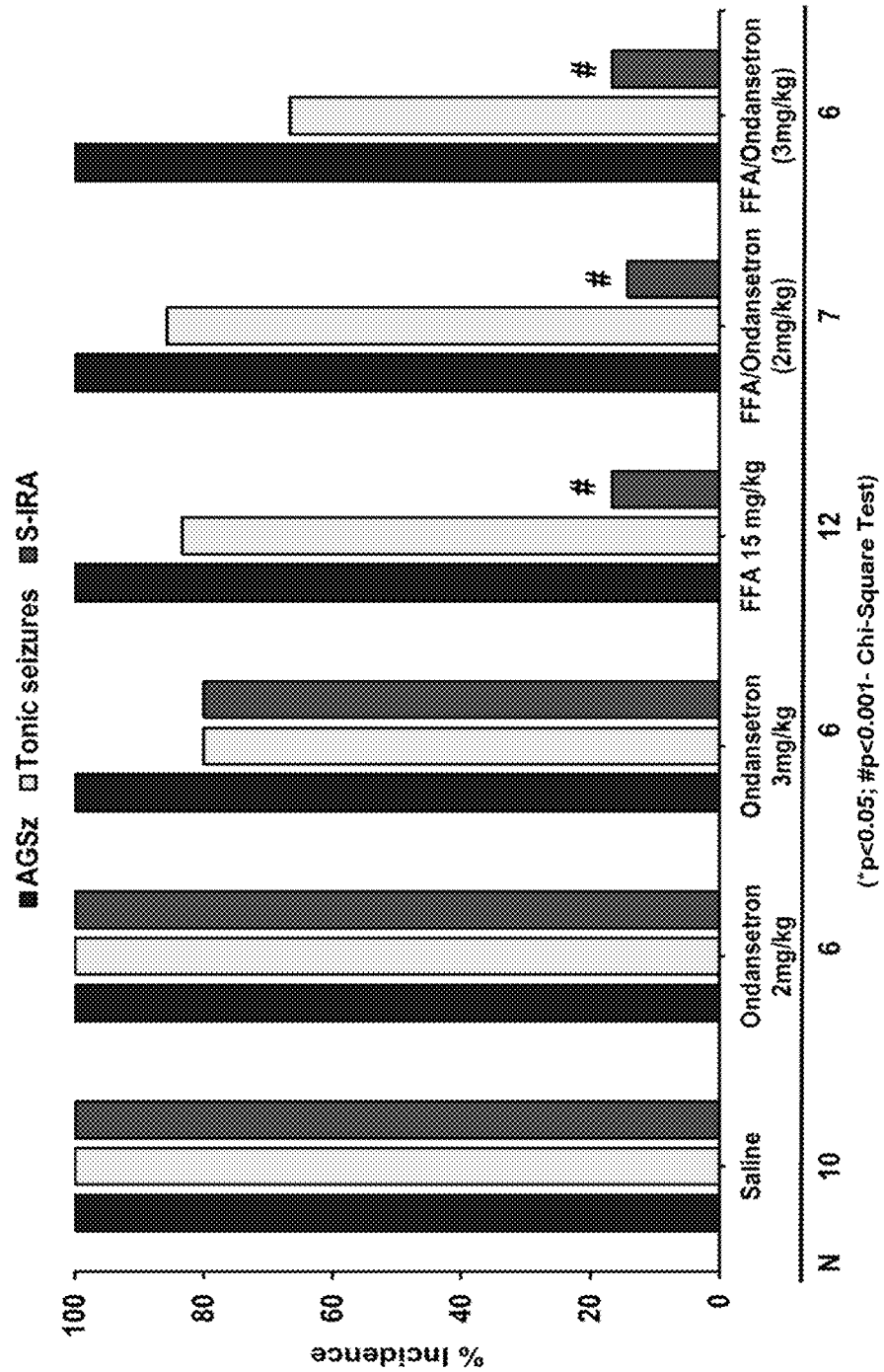

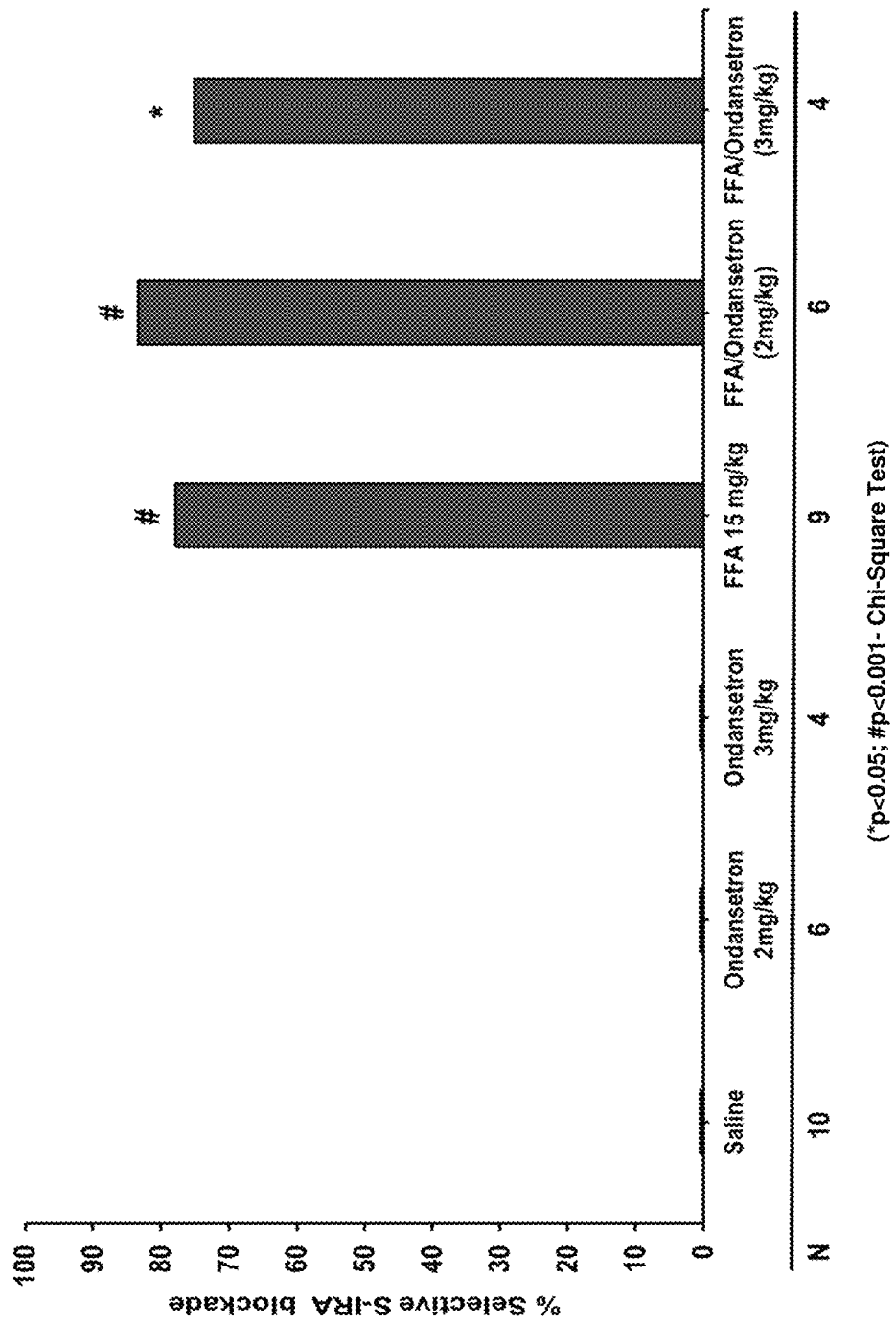

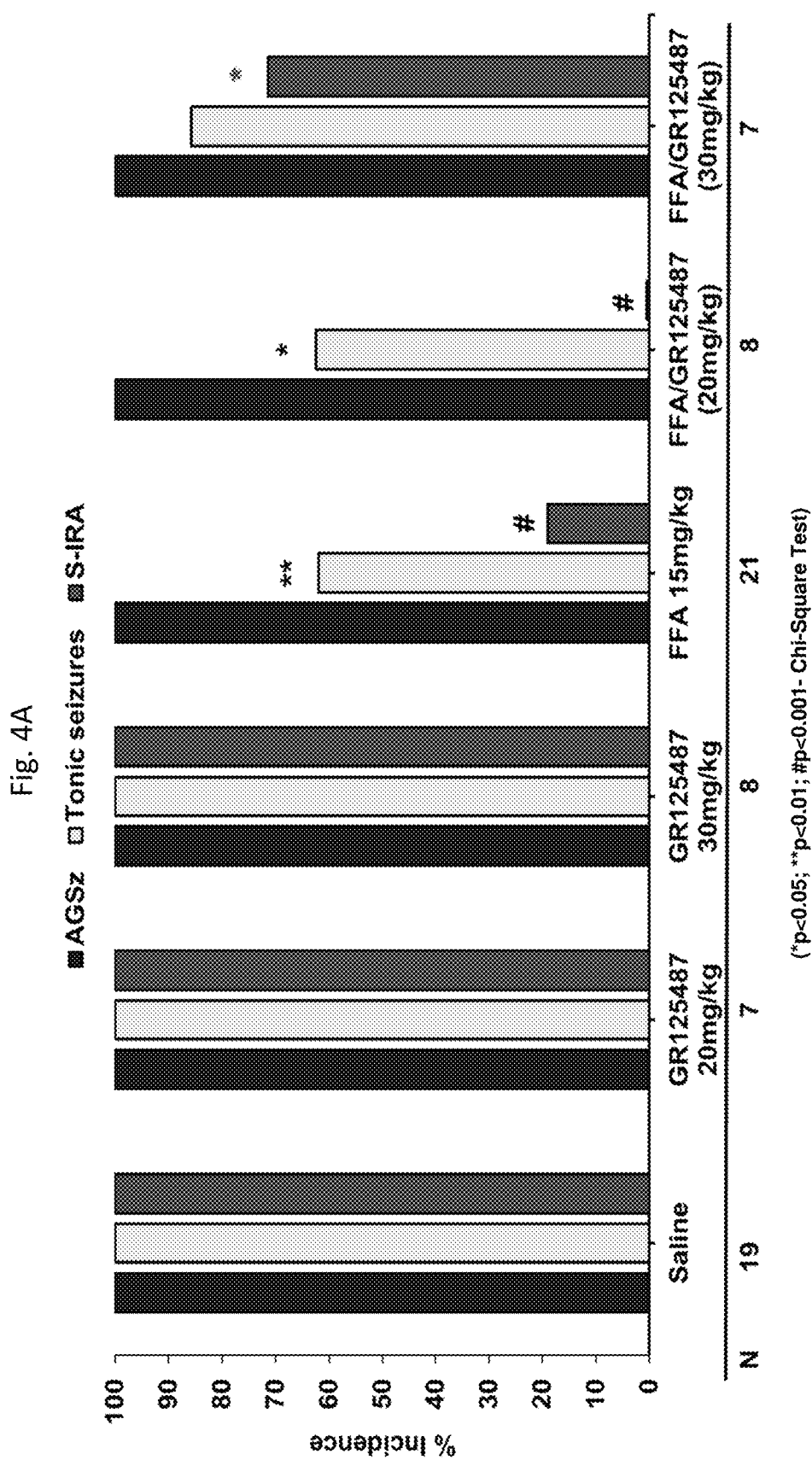

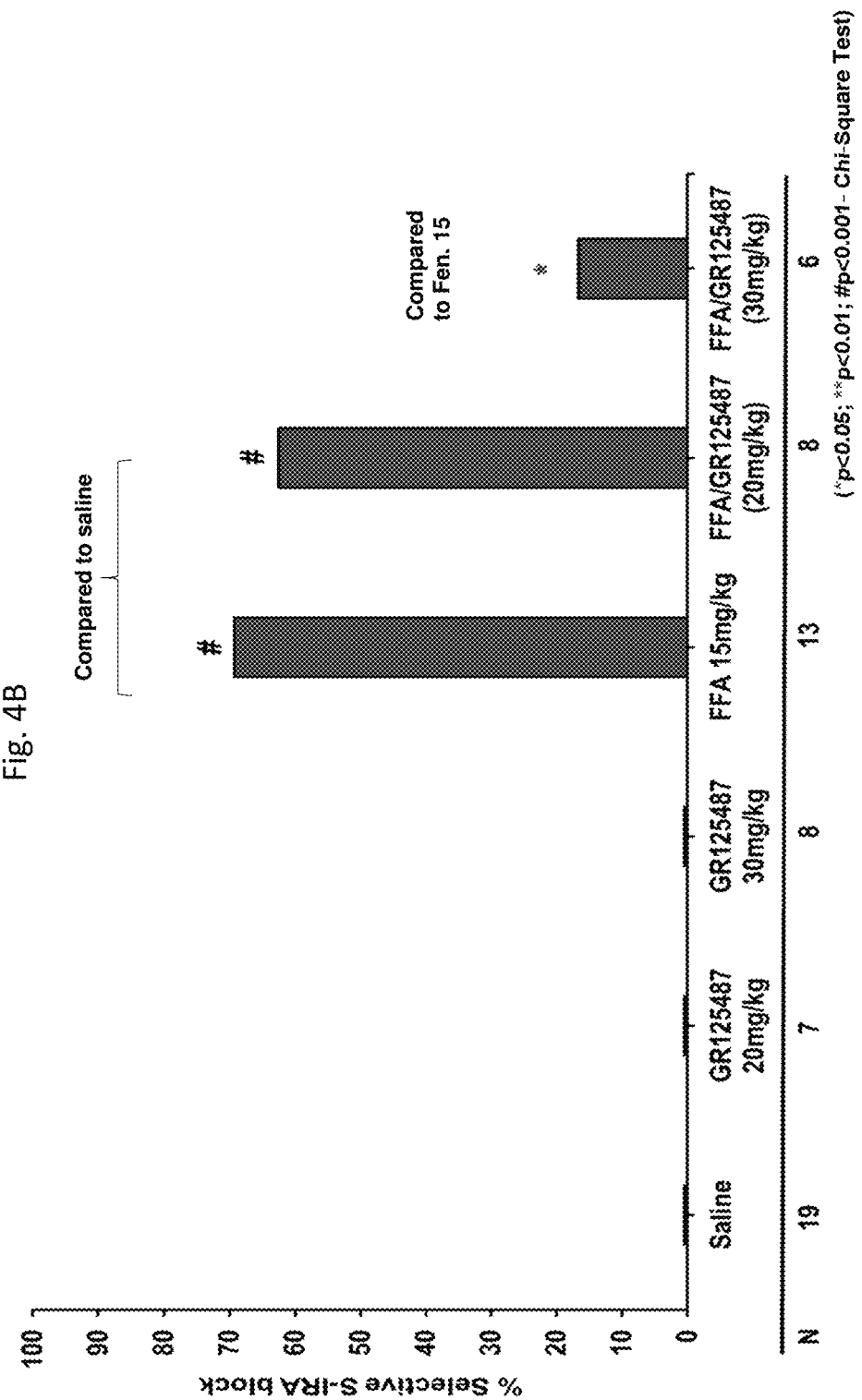

COMPOSITIONS AND METHODS FOR TREATING RESPIRATORY DEPRESSION WITH FENFLURAMINE

CROSS-REFERENCE TO RELATED APPLICATIONS

This application is a divisional of U.S. patent application Ser. No. 16/432,468 filed Jun. 5, 2019, now issued U.S. Pat. No. 10,517,841, issued Dec. 31, 2019 which claims the benefit of priority to U.S. Provisional Patent Application Ser. No. 62/685,200 filed Jun. 14, 2018, all of which applications are incorporated herein in their entirety.

FIELD

The present invention relates generally to the therapeutic treatment of a subject at risk of or undergoing respiratory distress, such as is induced by opiates, barbiturates, and benzodiazepines. More specifically, the invention relates to the use of a 5-HT$_4$ agonist (e.g., fenfluramine) as a therapeutic agent, and to methods of its use to treat human patients undergoing or at risk of respiratory depression.

INTRODUCTION

Opioids are substances, both natural and synthetic, that bind to opioid receptors in the brain (including antagonists). There are several receptor subtypes in this family, of which the more characterized are the delta, kappa and mu receptors. The delta and μ$_2$ subtypes may modulate μ-opioid receptor-mediated respiratory depression.

Opiates are alkaloid compounds naturally found in the opium poppy plant *Papaver somniferum*. The psychoactive compounds found in the opium plant include morphine, codeine, and thebaine. There are also purely synthetic opioids such as, for example, tramadol (Ultram) and fentanyl (Actiq, Sublimaze) among others which are opioid-like medications.

All opioids, like opiates, are considered drugs of high abuse potential and are listed on various "Substance-Control Schedules" under the Uniform Controlled Substances Act of the United States of America. In 2013, between 13 and 20 million people used opiates recreationally (0.3% to 0.4% of the global population between the ages of 15 and 65) ("Status and Trend Analysis of Illicit [sic] Drug Markets." World Drug Report 2015).

By way of example, thebaine (paramorphine), also known as codeine methyl enol ether, is an opiate alkaloid. A minor constituent of opium, thebaine is chemically similar to both morphine and codeine, but has stimulatory rather than depressant effects. While thebaine is not used therapeutically, it is the main alkaloid extracted from *Papaver bracteatum* (Iranian poppy) and can be converted industrially into a variety of compounds, including oxycodone, oxymorphone, nalbuphine, naloxone, naltrexone, buprenorphine and etorphine. Butorphanol can also be derived from thebaine.

Sufentanil (R30730, brand name Sufenta) is a synthetic opioid analgesic drug approximately 5 to 10 times more potent than its parent drug, fentanyl, and 500 times as potent as morphine.

Tapentadol (brand names: Nucynta, Palexia and Tapal) is a centrally acting opioid analgesic of the benzenoid class with a dual mode of action as an agonist of the μ-opioid receptor and as a norepinephrine reuptake inhibitor (NRI). Analgesia occurs within 32 minutes of oral administration, and lasts for 4-6 hours.

Opioids are widely used analgesics in anesthesiology. However, opioids also have serious adverse effects, such as depression of breathing. In fact, many different drugs have been found to be associated with increased risk of respiratory depression. Strong opioids (e.g., fentanyl, heroin, or morphine), some barbiturates, and some benzodiazepines (e.g., short acting ones and alprazolam) are known for depressing respiration. Overdosing on these drugs can cause an individual to cease breathing entirely (go into respiratory arrest) which is rapidly fatal without treatment.

Furthermore, concomitant use of benzodiazepines and opioids may result in profound sedation, respiratory depression, coma, and death. Thus, physicians are typically instructed not to prescribe the two together, to reserve concomitant prescribing of these drugs for use only in patients for whom alternative treatment options are inadequate and/or to limit dosages and durations to the minimum required and follow patients for signs and symptoms of respiratory depression and sedation.

Although the list below is not comprehensive, it is believed to include several barbiturates, benzodiazepines, opiates and other drugs which are widely prescribed and/or used recreationally.

TABLE 1

Common Drugs (e.g., Barbiturates and Benzodiazepines, Opiates, etc.) Associated with Risk of Respiratory Depression

| Drug class | Generic Name | Trade Name |
|---|---|---|
| Barbiturate | amobarbital sodium | Amytal Sodium |
| | aprobarbital, aprobarbitone | Oramon, Somnifaine, Allonal, Alurate |
| | butobarbital, butabarbital, butabarbital sodium | Butalan, Butisol, Butisol sodium, Buticaps, Sarisol |
| | methylophenobarbital, mephobarbital, mephobarbitone | Mebaral, Phemiton, Prominal, Mephyltaletten |
| | metharbital, endiemal, metharbitone, methobarbitone | Gemonil |
| | methohexital, methohexitone | Brietal, Brevital |
| | pentothal | Thiopental sodium |
| | phenobarbital, pentobarbital, pentobarbitone | Luminal, Nembutal, Nembutal sodium, Solfoton |
| | primidone, desoxyphenobarbital, desoxyphenobarbitone | Lepsiral, Mysoline, Resimatil, Primaclone |

TABLE 1-continued

Common Drugs (e.g., Barbiturates and Benzodiazepines, Opiates, etc.) Associated with Risk of Respiratory Depression

| Drug class | Generic Name | Trade Name |
|---|---|---|
| | secobarbital | Seconal |
| | thiamylal | Surital |
| Benzodiazepine | alprazolam | Xanax, Xanax XR |
| | carbamazepine | Carbatrol, Epitol, Equetro, Tegretol |
| | chlordiazepoxide | Librium |
| | clobazam | Frisium, Onfi |
| | clonazepam | Klonopin |
| | clorazepate | Tranxene |
| | diazepam | Diastat, Diastat Acudial, Diazepam Intensol, Valium |
| | estazolam | Prosom |
| | ethyl loflazepate | Meilax, Ronlax, Victan |
| | flunitrazepam | Rohypnol |
| | lorazepam | Ativan |
| | oxazepam | Zaxopam, Serax |
| | temazepam | Restoril |
| | triazolam | Halcion |
| Other | tramadol | Ultram, Zytram, Conzip |
| | gabapentin | Gralise, Horizant, Neurontin, Gabarone |
| | pregablin | Lyrica |
| | ketamine | Ketalar |
| | fosphenytoin | Cerebyx |
| | Phenytoin, diphenylhydantoin | Dilantin, Phenytek, and Epanutin |
| | Mephenytoin, 5-Ethyl-3-Methyl-5-Phenylhydantoin, Mefenetoin, Methoin, Methyl Phenetoin, Phenantoin, Phenetoin Methyl | Mesantoin |
| | mesuximide, methsuximide | Petinutin |
| | ethosuximide | Zarontin |
| | felbamate | Felbatol |
| | eslicarbazepine acetate | Aptiom |
| | oxcarbazepine | Trileptal, Oxtellar |
| | perampanel | Fycompa |
| | Ezogabine, retigabine | Potiga |
| | tiagabine | Gabitril |
| | topirimate | Topamax |
| | valproate, valproic acid, 2-propylvaleric acid, sodium valproate, valproate semisodium | Absenor, Convulex, Depakene, Depakine, Depalept, Deprakine, Divalproex, Encorate, Epival, Epilim, Stavzor, Valcote, Valpakine, Orfiril |
| | vigabatrin | Sabril |
| | lacosamide | Vimpat |
| | zonisamide | Zonegran |
| | acetaminophen/butalbital | Anolor 300, Bupap, Capacet, Cephadyn, Dolgic LQ, Esgic, Esgic-Plus, Ezol, Fioricet, Geone, Margesic, Orbivan CF, Phrenilin, Phrenilin Forte, Zebutal |
| | acetaminophen/hydrocodone | Vicodin, Norco, Lorcet |

For example, clobazam is in a class of medications called benzodiazepines. Clobazam (brand names Frisium, Urbanol, Onfi and Tapclob) has been marketed as an anxiolytic since 1975 and an anticonvulsant since 1984. Overdose and intoxication with clobazam can lead to CNS depression, associated with drowsiness, confusion and lethargy, sometimes progressing to ataxia, respiratory depression, hypotension and even coma or death. The risk of a fatal outcome is increased in cases of combined poisoning with other CNS depressants, including alcohol. (Wildin, et al., (1990). "Respiratory and sedative effects of clobazam and clonazepam in volunteers." *British Journal of Clinical Pharmacology.* 29(2):169-77).

Opioid-induced respiratory depression is dangerous and often fatal. Furthermore, an optimum treatment for respiratory depression has yet to be established. Thus, there is a dire, long felt, but previously unmet need for therapeutic agents effective in treating, preventing or ameliorating the respiratory depression that occurs in subjects taking opioids, barbiturates and/or benzodiazepines. The present disclosure has applicability to treatment, prevention, or amelioration of respiratory depression often induced by opioids, barbiturates and/or benzodiazepines, whether administered as therapeutic agents by doctors or hospitals, or taken illicitly by drug abusers or addicts.

BRIEF SUMMARY

Provided in the present disclosure is the surprising discovery that certain serotonin receptors (also known as 5-hydroxytryptamine (5-HT) receptors) mediate the action of fenfluramine (FFA) in blocking seizure-induced sudden death in mice. Specifically, agonists of the $5-HT_4$ receptor are useful in treating, reducing and/or ameliorating the risk or occurrence of respiratory depression associated with use of one or more opioids, barbiturates and/or benzodiazepines in a human patient.

The methods disclosed herein are generally useful for treating, preventing or ameliorating respiratory depression and/or seizure-induced respiratory arrest (S-IRA) associated with use of one or more opioids, barbiturates and/or benzodiazepines.

In some aspects, provided herein is a method of method of treating respiratory depression caused by one or more opioids, barbiturates and/or benzodiazepines in a human patient, comprising administering to the patient a therapeutically effective dose of a 5-hydroxytryptamine receptor 4 agonist (5-HT$_4$ agonist), and allowing the 5-HT$_4$ agonist to stimulate 5-HT$_4$ receptors in the patient, thereby treating respiratory depression caused by the opioid in the patient.

In some aspects, provided herein is a method of preventing respiratory depression and/or seizure-induced respiratory arrest (S-IRA) in a human patient being treated with an opioid, comprising administering to the patient a therapeutically effective dose of a 5-HT$_4$ agonist, and allowing the 5-HT$_4$ agonist to stimulate 5-HT$_4$ receptors in the patient, thereby preventing respiratory depression and/or S-IRA in the patient being treated with the opioid.

In some aspects, provided herein is a method of reducing incidence of respiratory depression caused by an opioid in a selected human patient population, comprising selecting a population of human patients being treated with an opioid and thereby at risk of respiratory depression, administering to the selected patient population a therapeutically effective dose of a 5-HT$_4$ agonist, and allowing the 5-HT$_4$ agonist to stimulate 5-HT$_4$ receptors in the selected patient population, thereby reducing incidence of respiratory depression caused by the opioid in the patient population.

In some aspects, provided herein is a method of reducing likelihood of respiratory depression caused by an opioid in a human patient, comprising selecting a human patient being treated with an opioid and thereby at risk of respiratory depression, administering to the patient a therapeutically effective dose of a 5-HT$_4$ agonist, and allowing the 5-HT$_4$ agonist to stimulate 5-HT$_4$ receptors in the patient, thereby reducing the likelihood of respiratory depression caused by an opioid in the patient in the patient.

In some aspects, provided herein is a method of stimulating one or more 5-HT$_4$ receptors in the brain of a patient undergoing treatment with an opioid, wherein the patient is at risk of respiratory depression, comprising administering a therapeutically effective dose of a 5-HT$_4$ agonist to the patient undergoing treatment with an opioid, and allowing the 5-HT$_4$ agonist to stimulate 5-HT$_4$ receptors in the brain of the patient undergoing treatment with an opioid, thereby reducing the risk of respiratory depression in the patient.

In some aspects, provided herein is a method of reducing respiratory depression in a patient treated with an opioid, comprising administering to the patient a therapeutically effective dose of a 5-hydroxytryptamine receptor 4 agonist (5-HT$_4$ agonist), and allowing the 5-HT$_4$ agonist to stimulate 5-HT$_4$ receptors in the patient, and thereby reducing respiratory depression in the patient treated with the opioid.

In some aspects, provided herein is a method of reducing opioid-induced respiratory depression in a human patient, comprising administering to the patient suffering from opioid-induced respiratory depression a therapeutically effective dose of a 5-HT$_4$ agonist, and allowing the 5-HT$_4$ agonist to stimulate 5-HT$_4$ receptors in the patient, thereby preventing respiratory depression in the patient being treated with opioids.

In some aspects, provided herein is a method of increasing the safety of administering benzodiazepines or barbiturates to a patient suffering from epilepsy, comprising administering an effective dose of a 5-HT$_4$ agonist along with the benzodiazepine or barbiturate, thereby lowering a risk of respiratory depression in the patient.

In some aspects, provided herein is a method of lowering a risk of respiratory depression associated with concomitant use of (i) an opioid and (ii) a barbiturate and/or benzodiazepine, comprising administering an effective dose of a 5-HT$_4$ agonist along with the opioid and the benzodiazepine and/or barbiturate, thereby lowering the risk of respiratory depression in the patient.

In some embodiments of the method, the 5-HT$_4$ agonist is selected from the group consisting of fenfluramine, BIMU-8, Cisapride, Mosapride, Prucalopride, Renzapride, RS-67506, Tegaserod, Zacopride, Metoclopramide, and Sulpiride or a pharmaceutically acceptable salt thereof.

In some embodiments of the method, the 5-HT$_4$ agonist is fenfluramine, or a pharmaceutically acceptable salt thereof.

In some embodiments, the fenfluramine is administered as an adjunctive therapeutic agent.

In some embodiments, the therapeutically effective dose of fenfluramine is selected from the group consisting of 0.1 mg/kg/day to 1.0 mg/kg/day up to a 30 mg maximum daily dose.

In some embodiments of the method, an effective dose is less than 10.0 mg/kg/day, or less than 1.0 mg/kg/day, or approximately 0.8 mg/kg/day, or approximately 0.5 mg/kg/day, or approximately 0.2 mg/kg/day, or approximately 0.1 mg/kg/day; or approximately 0.01 mg/kg/day. In some embodiments of the method, the effective dose of fenfluramine is 0.5 mg/kg/day. In some embodiments of the method, the effective dose of fenfluramine is between 0.01 mg/kg/day and 0.8 mg/kg/day.

In some embodiments of the method, the therapeutically effective dose of fenfluramine is administered in a dosage form selected from the groups consisting of oral, injectable, transdermal, inhaled, nasal, rectal, vaginal and parenteral.

In some embodiments of the method, the therapeutically effective dose of fenfluramine is administered in an oral liquid dosage form.

In some embodiments, the dosage form is an oral composition in an amount selected from the group consisting of 30 mg/day or less, 20 mg/day or less, 10 mg/day or less and 5 mg/day or less.

In some embodiments of the method, an effective dose of the 5-HT4 agonist is administered in a pharmaceutically acceptable carrier.

In some embodiments of the method, the fenfluramine is formulated with a pharmaceutically acceptable carrier.

In some embodiments of the method, the fenfluramine is the sole (only) pharmaceutically active drug administered to the patient.

In some embodiments of the method, the opioid is selected from the group consisting of buprenorphine, codeine, Demerol, Duramorph, fentanyl (Actiq, Duragesic), heroin, hydrocodone (Zohydro ER), hydromorphone (Dilaudid, Exalgo), Lorcet, methadone, morphine (Avinza, Kadian, MSIR, MSContin), Norco, oxycodone (OxyContin, Roxicodone), oxymorphone (Opana ER), Palladone, Percodan, Percocet, remifentanil, Roxanol, Sublimaze, sufentanil (R30730, Sufenta), tapentadol (Nucynta, Palexia, Tapal), tramadol (Ultram), Tylox, and Vicodin, or a pharmaceutically acceptable salt thereof.

In some embodiments of the method, the opioid is fentanyl (Actiq, Duragesic), remifentanil, or sufentanil (R30730, Sufenta), or a pharmaceutically acceptable salt thereof.

In some embodiments of the method, the 5-HT$_4$ agonist further counteracts the intensifying effects of ethanol or other CNS depressants on respiratory depression that are ingested or present with the opiate, barbiturate or benzodiazepine that further potentiate the respiratory depression.

In some embodiments of the method, the 5-HT$_4$ agonist is at least one of:
(a) inactive at the 5-HT$_{2B}$ receptor;
(b) a neutral agonist of the 5-HT$_{2B}$ receptor; and
(c) an inverse agonist of the 5-HT$_{2B}$ receptor 5-HT$_{2B}$ receptor.

In some embodiments, the patient exhibits a significantly higher responder rate compared with placebo.

In some embodiments, the method further includes repeating the administering over a period of days until the patient exhibits a ≥40% reduction from baseline in occurrence of respiratory depression.

In some embodiments, the patient exhibits at least a ≥50% reduction in occurrence of respiratory depression.

In some embodiments, the patient exhibits at least a ≥75% reduction in occurrence of respiratory depression.

In some embodiments, the patient exhibits at least a ≥90% reduction in occurrence of respiratory depression.

In some embodiments, the patient is completely free of an occurrence of respiratory depression.

In some embodiments, the patient is alive after two years after first administration of the 5-HT$_4$ agonist.

In some embodiments of the method, the 5-HT$_4$ agonist is in a formulation adapted to a dosage forms selected from the group consisting of an oral dosage form, an intravenous dosage form, rectal dosage form, subcutaneous dosage form, and a transdermal dosage form.

In some embodiments of the method, the oral dosage form is selected from the group consisting of a liquid, a suspension, a tablet, a capsule, a lozenge, and a dissolving strip.

In some embodiments of the method, the 5-HT$_4$ agonist is administered prior to dosing with a benzodiazepine or barbiturate.

In some embodiments of the method, the 5-HT$_4$ agonist is administered at substantially the same time as dosing with a benzodiazepine or barbiturate.

In some embodiments of the method, the benzodiazepine or barbiturate is selected from the group consisting of those drugs appearing in Table 1.

In another aspect, the disclosure provides a kit comprising a therapeutic agent, e.g., a 5-HT$_4$ agonist, as used in any of the methods disclosed herein, and instructions for use.

As shown above and as will be recognized by others skilled in the art, the therapeutic agents provide the important advantage that they are more effective and/or exhibit an improved safety profile as compared to other therapeutic agents and methods currently known in the art.

These and other objects, advantages, and features of the invention will become apparent to those persons skilled in the art upon reading the details of the therapeutic agents and methods of using the same as are more fully described below.

BRIEF DESCRIPTION OF THE DRAWINGS

The invention is best understood from the following detailed description when read in conjunction with the accompanying drawings. Included in the drawings are the following figures:

FIGS. 1A-1D: show the dose- and time-dependent effects of fenfluramine (FFA) on incidence of tonic seizures and seizure-induced respiratory arrest (S-IRA) in the DBA/1 mouse model.

FIGS. 2A-2B: demonstrate that a 5-HT$_2$ receptor antagonist (Ritanserin) reversed the anticonvulsant effect of FFA on seizures and S-IRA in DBA/1 mice.

FIGS. 3A-3B: demonstrate that a 5-HT$_3$ receptor antagonist (Ondansetron) did not reverse the anticonvulsant effects of FFA on seizures or S-IRA in DBA/1 mice.

FIGS. 4A-4B: demonstrate that a 5-HT$_4$ receptor antagonist (GR125487) reversed the anticonvulsant and S-IRA blocking effects of FFA in DBA/1 mice.

DETAILED DESCRIPTION

Figure 1D:
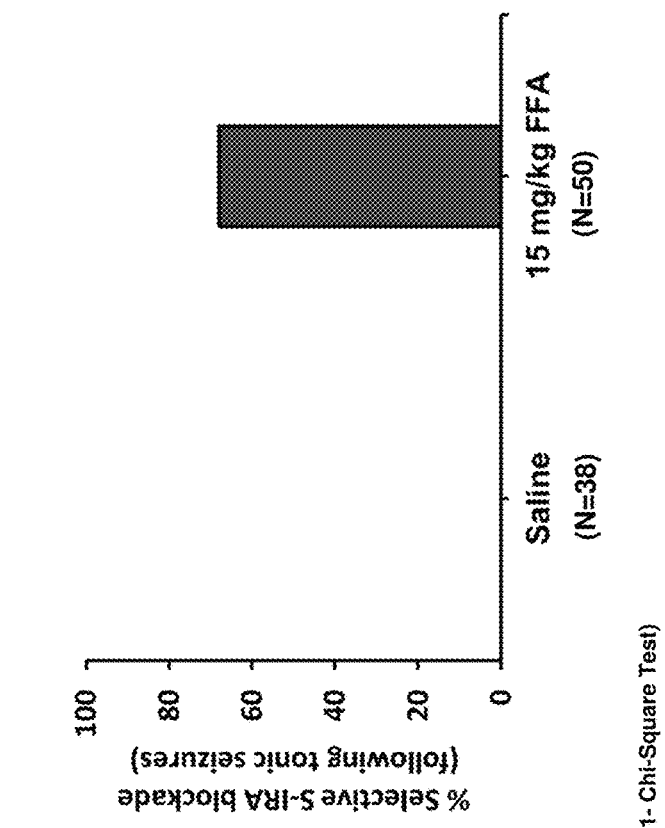

Before the present compositions and methods are described, it is to be understood that this invention is not limited to the particular formulations and methods described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges can independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those include limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims the singular forms "a," "an," and "the" include plural referents unless the context clearly dictates otherwise.

Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing of the present application. Nothing herein is to be construed as an admission that the present invention is not entitled to antedate such publication by virtue of prior invention. Further, the dates of publication provided may be different from the actual publication dates which may need to be independently confirmed.

Fifteen years ago, it was reported that 5-HT$_4$a receptors are strongly expressed in respiratory neurons of the brainstem, and that treatment of rats with the 5-HT$_4$ receptor agonist BIMU8 counteracted fentanyl-induced respiratory depression (Manzke et al., 2003, Science. 301(5630):226-9; incorporated herein by reference in its entirety).

Recently, we discovered that fenfluramine (FFA) acts at specific 5-HT receptors, including the 5-HT$_4$ receptor, to block seizure-induced respiratory arrest (S-IRA) in the DBA/1 mouse model of Sudden Unexpected Death in Epilepsy (SUDEP). Specific serotonin receptor subtypes were found to mediate this action of fenfluramine in blocking seizure-induced sudden death and seizure-induced respiratory arrest (S-IRA).

The present disclosure is directed to the surprising discovery that certain serotonin receptors (also known as 5-hydroxytryptamine (5-HT) receptors) mediate the action of fenfluramine (FFA) in blocking seizure-induced sudden death and seizure-induced respiratory arrest (S-IRA) in mice. Specifically, agonists of the 5-HT$_4$ receptor are useful in treating, reducing and/or ameliorating the risk or occurrence of respiratory depression associated with use of one or more opioids, barbiturates and/or benzodiazepines in a human patient.

Recently it was discovered that the intractable seizures characteristic of Dravet syndrome can be significantly reduced in frequency and/or severity, and in some cases eliminated entirely, by administering the drug 3-trifluoromethyl-N-ethylamphetamine (hereinafter "fenfluramine"). See Ceulemans et. al., Successful use of fenfluramine as an add-on treatment for Dravet Syndrome, Epilepsia 53(7): 1131-1139, 2012. Fenfluramine, is an amphetamine derivative having the following structure:

Structure 1

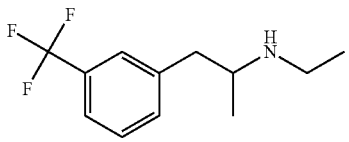

(R,S)-N-ethyl-1-[3-(trifluoromethyl)phenyl]propan-2-amine

Fenfluramine is a racemic mixture of two enantiomers, dexfenfluramine and levofenfluramine, and has been reported to increase the circulating levels of serotonin, a neurotransmitter that regulates mood, appetite and other functions.

Serotonin (also known as "5-hydroxytryptamine" or "5-HT") is a monoaminergic neurotransmitter believed to modulate numerous sensory, motor and behavioral processes in the mammalian nervous system. Diverse responses are elicited through the activation of a large family of receptor subtypes. Of the many subtypes of serotonin receptors, the 5-HT$_{1B}$ and 5-HT$_{2C}$ subtypes are most strongly implicated in modulating feeding and body weight, and these receptors are expressed in hypothalamic regions believed to be involved in food intake regulation. Fenfluramine was known to have high affinity for and activity at the 5-HT$_{2A}$, 5-HT$_{2B}$ and 5-HT$_{2C}$ receptor subtypes (Rothman et al, 2015), and because 5-HT$_{2C}$-agonists trigger appetite suppression, fenfluramine was used for treating obesity by co-administering it together with phentermine as part of the popular weight loss drug combination treatment marketed as Fen-Phen (i.e., fenfluramine/phentermine). Fen-Phen was first marketed in the US in 1973 to prevent and treat obesity, but in 1997, Fen-Phen was withdrawn from the US and global markets, as its use was associated with the onset of cardiac valvulopathy and pulmonary hypertension.

The adverse effects associated with the use of Fen-Phen as an anorexic agent were believed to be attributable to the interaction of fenfluramine's primary metabolite norfenfluramine with the 5-HT$_{2B}$ receptor, the activation of which was associated with cardiac valvulopathy. It was for this reason that Fen-Phen was withdrawn from the market and is no longer indicated for use in any therapeutic area.

Despite past cardiovascular safety concerns that arose when high doses of fenfluramine were used for treatment of adult obesity, attempts have been made to identify further therapeutic uses for that product, while weighing the known cardiovascular risks of fenfluramine against potential therapeutic benefits. The present disclosure provides a new treatment option for reversing respiratory depression often induced by opioids, barbiturates and/or benzodiazepines.

One use for fenfluramine is the treatment, amelioration and/or prevention of seizures, such as in epilepsy and epileptic encephalopathies. Sudden Unexpected Death in Epilepsy (SUDEP) is a major cause of increased premature mortality that disproportionally affects young persons with epilepsy. Witnessed SUDEP cases often observed generalized tonic-clonic seizures (GTC) leading to respiratory and cardiac failure during post-ictal behavioral depression (PID). The leading risk factors of SUDEP include male sex, GTC, young age, and high seizure frequency. Approaches to reducing SUDEP incidence include improved medication compliance, nocturnal monitoring, mitigating respiratory compromise and responsive neurostimulation (Devinsky et al., 2018, Epilepsia 59:555-561; Rugg-Gunn et al., Epilepsia 57 Suppl 1:26-34, 2016). SUDEP is known to be associated with subtherapeutic levels of antiepileptic drugs (AEDs) and addition of AEDs can reduce the incidence of SUDEP in drug resistant epilepsy (George and Davis. J Forensic Sci. 43:598-603, 1998; Ryvlin et al., 2013, Lancet Neurol. 12:966-77). Therefore, there is a vital need for add-on AEDs with an indication for SUDEP prophylaxis.

DBA/1 mice are a widely-used rodent model that recapitulates many aspects of human SUDEP. DBA/1 mice exhibit increased susceptibility to seizure and seizure-induced respiratory arrest and death (S-IRA) in response to electroconvulsive shock, hyperthermia, convulsant drug and intense acoustic stimulation (audiogenic seizures, AGSz) (Deckard et al., 1976, Developmental psychobiology 9:17-24; Faingold, et al., 2011, Epilepsy Behav. 22:186-190; Faingold, et al., 2016, Epilepsy Behav. 64(Pt A):166-170; Löscher et al., 2017, Epilepsy Behav. 73:214-235; Maxson S. C., 1980, Epilepsia 21, 637-645). The AGSz in DBA/1 mice comprise of GTC followed by S-IRA during PID. Serotonin (5-hydroxytryptamine, 5-HT) is an important neurotransmitter released during PID that modulates respiration (Murugesan et al., Epilepsia 59:e91-e97, 2018; Hilaire et al., 2010, Respir. Physiol. Neurobiol. 174(1-2):76-88; Zhang et al., Neurobiology of disease 110:47-58).

Abbreviations used throughout this disclosure include:
5-HT 5-hydroxytryptamine
AGSz Audiogenic seizures
FFA Fenfluramine, 5-HT release enhancer
GTC Generalized tonic-clonic seizures
i.p. intraperitoneal
N Number of animals
PID Post-ictal depression
SUDEP Sudden Unexpected Death in Epilepsy
S-IRA Seizure-induced respiratory arrest
SSRI Selective serotonin reuptake inhibitor Provided in the present disclosure is the surprising discovery that certain serotonin receptors (also known as 5-hydroxytryptamine (5-HT) receptors) mediate the action of fenfluramine (FFA) in blocking seizure-induced sudden death in mice. Specifically, agonists of the 5-HT$_4$ receptor are useful in treating, reducing and/or ameliorating the risk or occurrence of respiratory depression associated with use of one or more opioids, barbiturates and/or benzodiazepines in a human patient.

The methods disclosed herein are generally useful for treating, preventing or ameliorating respiratory depression and/or seizure-induced respiratory arrest (S-IRA) associated with use of one or more opioids, barbiturates and/or benzodiazepines.

In some aspects, provided herein is a method of method of treating respiratory depression caused by an opioid in a human patient, comprising administering to the patient a therapeutically effective dose of a 5-hydroxytryptamine receptor 4 agonist (5-HT$_4$ agonist), and allowing the 5-HT$_4$ agonist to stimulate 5-HT$_4$ receptors in the patient, thereby treating respiratory depression caused by the opioid in the patient.

In some aspects, provided herein is a method of preventing respiratory depression and/or seizure-induced respiratory arrest (S-IRA) in a human patient being treated with an opioid, comprising administering to the patient a therapeutically effective dose of a 5-HT$_4$ agonist, and allowing the 5-HT$_4$ agonist to stimulate 5-HT$_4$ receptors in the patient, thereby preventing respiratory depression and/or S-IRA in the patient being treated with the opioid.

In some aspects, provided herein is a method of reducing incidence of respiratory depression caused by an opioid in a selected human patient population, comprising selecting a population of human patients being treated with an opioid and thereby at risk of respiratory depression, administering to the selected patient population a therapeutically effective dose of a 5-HT$_4$ agonist, and allowing the 5-HT$_4$ agonist to stimulate 5-HT$_4$ receptors in the selected patient population, thereby reducing incidence of respiratory depression caused by the opioid in the patient population.

In some aspects, provided herein is a method of reducing likelihood of respiratory depression caused by an opioid in a human patient, comprising selecting a human patient being treated with an opioid and thereby at risk of respiratory depression, administering to the patient a therapeutically effective dose of a 5-HT$_4$ agonist, and allowing the 5-HT$_4$ agonist to stimulate 5-HT$_4$ receptors in the patient, thereby reducing the likelihood of respiratory depression caused by an opioid in the patient in the patient.

In some aspects, provided herein is a method of stimulating one or more 5-HT$_4$ receptors in the brain of a patient undergoing treatment with an opioid, wherein the patient is at risk of respiratory depression, comprising administering a therapeutically effective dose of a 5-HT$_4$ agonist to the patient undergoing treatment with an opioid, and allowing the 5-HT$_4$ agonist to stimulate 5-HT$_4$ receptors in the brain of the patient undergoing treatment with an opioid, thereby reducing the risk of respiratory depression in the patient.

In some aspects, provided herein is a method of reducing respiratory depression in a patient treated with an opioid, comprising administering to the patient a therapeutically effective dose of a 5-hydroxytryptamine receptor 4 agonist (5-HT$_4$ agonist), and allowing the 5-HT$_4$ agonist to stimulate 5-HT$_4$ receptors in the patient, and thereby reducing respiratory depression in the patient treated with the opioid.

In some aspects, provided herein is a method of reducing opioid-induced respiratory depression in a human patient, comprising administering to the patient suffering from opioid-induced respiratory depression a therapeutically effective dose of a 5-HT$_4$ agonist, and allowing the 5-HT$_4$ agonist to stimulate 5-HT$_4$ receptors in the patient, thereby preventing respiratory depression in the patient being treated with opioids.

In some aspects, provided herein is a method of increasing the safety of administering benzodiazepines or barbiturates to a patient suffering from epilepsy, comprising administering an effective dose of a 5-HT$_4$ agonist along with the benzodiazepine or barbiturate, thereby lowering a risk of respiratory depression in the patient.

In some aspects, provided herein is a method of lowering a risk of respiratory depression associated with concomitant use of (i) an opioid and (ii) a barbiturate and/or benzodiazepine, comprising administering an effective dose of a 5-HT$_4$ agonist along with the opioid and the benzodiazepine and/or barbiturate, thereby lowering the risk of respiratory depression in the patient.

In some embodiments of the method, the 5-HT$_4$ agonist is selected from the group consisting of fenfluramine, BIMU-8, Cisapride, Mosapride, Prucalopride, Renzapride, RS-67506, Tegaserod, Zacopride, Metoclopramide, and Sulpiride or a pharmaceutically acceptable salt thereof.

In some embodiments of the method, the 5-HT$_4$ agonist is fenfluramine, or a pharmaceutically acceptable salt thereof.

In some embodiments, the fenfluramine is administered as an adjunctive therapeutic agent.

In some embodiments, the therapeutically effective dose of fenfluramine is selected from the group consisting of 0.2 mg/kg/day to 0.08 mg/kg/day up to a 30 mg maximum daily dose.

In some embodiments of the method, an effective dose is less than 10.0 mg/kg/day, or less than 1.0 mg/kg/day, or approximately 0.8 mg/kg/day, or approximately 0.5 mg/kg/day, or approximately 0.2 mg/kg/day, or approximately 0.1 mg/kg/day; or approximately 0.01 mg/kg/day. In some embodiments of the method, the effective dose of fenfluramine is 0.5 mg/kg/day. In some embodiments of the method, the effective dose of fenfluramine is between 0.01 mg/kg/day and 0.8 mg/kg/day.

In some embodiments of the method, the therapeutically effective dose of fenfluramine is administered in a dosage form selected from the groups consisting of oral, injectable, transdermal, inhaled, nasal, rectal, vaginal and parenteral.

In some embodiments of the method, the therapeutically effective dose of fenfluramine is administered in an oral liquid dosage form.

In some embodiments, the dosage form is an oral composition in an amount selected from the group consisting of 30 mg/day or less, 20 mg/day or less, 10 mg/day or less and 5 mg/day or less.

In some embodiments of the method, an effective dose of the 5-HT4 agonist is administered in a pharmaceutically acceptable carrier.

In some embodiments of the method, the fenfluramine is formulated with a pharmaceutically acceptable carrier.

In some embodiments of the method, the fenfluramine is the sole (only) pharmaceutically active drug administered to the patient.

In some embodiments of the method, the opioid is selected from the group consisting of buprenorphine, codeine, Demerol, Duramorph, fentanyl (Actiq, Duragesic), heroin, hydrocodone (Zohydro ER), hydromorphone (Dilaudid, Exalgo), Lorcet, methadone, morphine (Avinza, Kadian, MSIR, MSContin), Norco, oxycodone (OxyContin, Roxicodone), oxymorphone (Opana ER), Palladone, Percodan, Percocet, remifentanil, Roxanol, Sublimaze, sufentanil (R30730, Sufenta), tapentadol (Nucynta, Palexia, Tapal), Tylox, and Vicodin, or a pharmaceutically acceptable salt thereof.

In some embodiments of the method, the opioid is fentanyl (Actiq, Duragesic), remifentanil, or sufentanil (R30730, Sufenta), or a pharmaceutically acceptable salt thereof.

In some embodiments, the method further comprises administering to the patient an effective dose of clobazam or a pharmaceutically acceptable salt thereof.

In some embodiments of the method, the 5-HT$_4$ agonist is at least one of:
(a) inactive at the 5-HT$_{2B}$ receptor;
(b) a neutral agonist of the 5-HT$_{2B}$ receptor; and
(c) an inverse agonist of the 5-HT$_{2B}$ receptor 5-HT$_{2B}$ receptor.

In some embodiments, the patient exhibits a significantly higher responder rate compared with placebo.

In some embodiments, the method further includes repeating the administering over a period of days until the patient exhibits a ≥40% reduction from baseline in occurrence of respiratory depression.

In some embodiments, the patient exhibits at least a ≥50% reduction in occurrence of respiratory depression.

In some embodiments, the patient exhibits at least a ≥75% reduction in occurrence of respiratory depression.

In some embodiments, the patient exhibits at least a ≥90% reduction in occurrence of respiratory depression.

In some embodiments, the patient is completely free of an occurrence of respiratory depression.

In some embodiments, the patient is alive after two years after first administration of the 5-HT$_4$ agonist.

In some embodiments of the method, the 5-HT$_4$ agonist is in a formulation adapted to a dosage forms selected from the group consisting of an oral dosage form, an intravenous dosage form, rectal dosage form, subcutaneous dosage form, and a transdermal dosage form.

In some embodiments of the method, the oral dosage form is selected from the group consisting of a liquid, a suspension, a tablet, a capsule, a lozenge, and a dissolving strip.

In some embodiments of the method, the 5-HT$_4$ agonist is administered prior to dosing with a benzodiazepine or barbiturate.

In some embodiments of the method, the 5-HT$_4$ agonist is administered at substantially the same time as dosing with a benzodiazepine or barbiturate.

In some embodiments of the method, the benzodiazepine or barbiturate is selected from the group consisting of those drugs appearing in Table 1.

In another aspect, the disclosure provides a kit comprising a therapeutic agent, e.g., a 5-HT$_4$ agonist, as used in any of the methods disclosed herein, and instructions for use.

Thus, the disclosure provides methods which employ certain therapeutic agents useful in treating patients having respiratory depression and/or seizure-induced respiratory arrest (S-IRA), who require treatment. The disclosure further provides methods which employ certain therapeutic agents useful in preventing, treating or ameliorating symptoms associated with respiratory depression and/or seizure-induced respiratory arrest (S-IRA) in a human patient being treated with at least one opioid, barbiturate and/or benzodiazepine.

The methods disclosed herein comprise administering a therapeutically effective amount of one or more therapeutic agents. A number of therapeutic agents can be employed in the methods of the present invention. In some embodiments, the therapeutic agent is a 5-HT$_4$ receptor agonist. In some embodiments, the therapeutic agent is active at one or more targets, or two or more targets, or three or more targets, or four or more targets, or five or more targets, or more. In some embodiments, the therapeutic agent activates the 5-HT$_4$ receptor. In some embodiments, the therapeutic agent activates the 5-HT$_2$ receptor. In some embodiments, the therapeutic agent activates the 5-HT$_7$ receptor.

The present disclosure provides a method of preventing, treating or ameliorating symptoms associated with respiratory depression and/or seizure-induced respiratory arrest (S-IRA) in a human patient being treated with at least one opioid, barbiturate and/or benzodiazepine, wherein the therapeutic agent is a compound that is active at one or more targets. In some aspects, the therapeutic agent comprises a compound that activates a 5-HT receptor protein such as an agonist of the 5-HT$_4$ receptor.

The disclosure further provides pharmaceutical compositions comprising one or more of the therapeutic agents disclosed herein for use in the methods of the invention. In some embodiments, the pharmaceutical compositions are formulations adapted to one or more dosage forms comprising an oral dosage form, an intravenous dosage form, rectal dosage form, subcutaneous dosage form, and a transdermal dosage form. In particular embodiments, the oral dosage forms are selected from the group consisting of a liquid, a suspension, a tablet, a capsule, a lozenge, and a dissolving strip. In one embodiment, the transdermal dosage form is a patch.

The disclosure further provides methods of preventing, treating or ameliorating one or more symptoms of respiratory distress, respiratory depression and/or seizure-induced respiratory arrest (S-IRA) associated with the use of opioids, barbiturates, and/or benzodiazepines.

In one embodiment, the method may also involve a patient being treated for status epilepticus. Status Epilepticus is a severe and intractable condition categorized as a medical emergency requiring immediate medical intervention, typically involving hospitalization. Status Epilepticus can be fatal. It can also be associated with cerebral hypoxia, possibly leading to damage to brain tissue.

In one embodiment, the disclosure provides methods of preventing, or reducing the incidence (frequency) of respiratory depression, seizure-induced respiratory arrest (S-IRA) or Sudden Unexpected Death in Epilepsy (SUDEP) in a population of human patients also being treated with at least one opioid, barbiturate and/or benzodiazepine. In some embodiments, the patient is obese.

Opioids

A non-exhaustive list of opioid includes, but is not limited to, buprenorphine, codeine, Demerol, Duramorph, fentanyl (Actiq, Duragesic), heroin, hydrocodone (Zohydro ER), hydromorphone (Dilaudid, Exalgo), methadone, morphine (Avinza, Kadian, MSIR, MSContin), oxycodone (OxyContin, Roxicodone), oxymorphone (Opana ER), Palladone, Percodan, Percocet, remifentanil, Roxanol, Sublimaze, sufentanil (R30730, Sufenta), tapentadol (Nucynta, Palexia, Tapal), Tylox, and Vicodin, or pharmaceutically acceptable salts thereof.

Opioid-containing pharmaceutical compositions used as pain medications include acetaminophen/hydrocodone (Vicodin, Norco, Lorcet); these may also cause respiratory depression.

Another pain medication that is associated with respiratory distress is gabapentin. Gabapentin (Neurontin) is a medication used to treat epilepsy (specifically partial seizures), neuropathic pain, hot flashes, and restless legs syndrome. Gabapentin has been associated with a rare risk of severe respiratory depression even without concomitant opioid medicines. Patients with compromised respiratory function, respiratory or neurological disease, renal impairment, concomitant use of central nervous system (CNS) depressants, and elderly people might be at higher risk of experiencing severe respiratory depression. Dose adjustments might be necessary in these patients.

Gabapentin is a gabapentinoid: it has a structure similar to the inhibitory neurotransmitter γ-aminobutyric acid (GABA); however, it crosses the blood-brain barrier more easily. It acts by inhibiting certain calcium channels. Gabapentinoids, also known as α2δ ligands, are a class of drugs that are derivatives of the inhibitory neurotransmitter γ-aminobutyric acid (GABA) (i.e., GABA analogues) which block α2δ subunit-containing voltage-dependent calcium channels (VDCCs). This site has been referred to as the gabapentin receptor (α2δ subunit), as it is the target of the drugs gabapentin and pregabalin.

Clinically-used gabapentinoids include gabapentin and pregabalin as well as a gabapentin prodrug, gabapentin enacarbil. In addition, phenibut has been found to act as a gabapentinoid in addition to its action of being a $GABA_B$ receptor agonist. Another analogue, mirogabalin, is in clinical trials, but has not yet been approved. Other gabapentinoids which are used in scientific research but have not been approved for medical use include atagabalin, 4-methylpregabalin and PD-217,014.

Barbiturates

Barbiturates are a class of drugs called central nervous system (CNS) depressants. When taken as prescribed, barbiturates help people sleep or with symptoms of anxiety. However, abuse of these medications can have fatal consequences. Because barbiturates are highly addictive, they present large risk of abuse and overdose.

The action of barbiturates on the CNS, directly affects nerve endings in the smooth muscles, lowering heart rate, respiration, and blood pressure. Long term and/or excessive use of barbiturates may result in respiratory depression. In the brain, barbiturates interact with neural channels and transmitters, inhibiting required responses, and quickly, with repeated use, tolerance occurs requiring more and more of the drug, to achieve desired results. Because barbiturates cross the 'brain-barrier' easily and readily dissolve into body fat, they will reenter the blood stream at different rates depending on various factors (such as body metabolism, other drugs already in system) or type of barbiturate used. Also, the liver helps metabolize this drug into soluble components, as it does for alcohol; overuse can cause hepatitis. These results makes use of this drug extremely dangerous, as its active levels in a user's body are very difficult to determine, and overdose is extremely likely, especially when combined with alcohol, other drugs, or opiates.

Barbiturates, categorically opposite to amphetamines (stimulants), act on the CNS (central nervous system) as a sedative-hypnotic drug, essentially 'depressing' its function within body and brain. Like amphetamines, barbiturates were synthesized near the turn of the 20th century, the first derivative being, Barbital, (brand names, Veronal or Medinal), developed by chemists at Bayer pharmaceuticals, in Germany, in 1903, soon followed by Phenobarbital, (Luminal), in 1912. Since then, with over 2500 derivatives (compounds) created, barbiturates are typically classified according to the 'speed of onset,' and 'duration of action,' starting with the 'ultra-short acting' group used in anesthesia, followed by the 'short/intermediate acting' group, used in anesthesia, and to calm and sedate, (now, benzodiazepines are usually applied), and lastly, the 'long-acting' barbiturates, where Phenobarbital is placed, with a half-life of 92 hours (almost 4 days), sometimes prescribed for convulsions. Like amphetamines, barbiturates, went unchecked for nearly fifty years being readily prescribed for tension, anxiety, insomnia, and extreme behavioral reactions. In the 1950's, the medical community ultimately acknowledged that serious mental and physical health risks could be associated with this depressant—life-threatening reactions when combined with other drugs; rapid tolerance and addiction; potential for lethal overdose.

Barbiturates are classified in four broad groups: ultra-short acting, short acting, intermediate acting and long acting. Ultra-short acting barbiturates are typically used in anesthesia, injected intravenously, and produce anesthetic results in one minute or less. Short acting to intermediate acting barbiturates achieve results in 15 to 40 minutes. Long acting barbiturates take effect in about an hour, and last about 12 hours.

Barbiturates—Brand Names:
Allonal (Aprobarbital or aprobarbitone), sold as Oramon, Somnifaine, and Allonal
Amytal Sodium (Amobarbital)
Brevital (Methohexital)
Butabarb
Butalan
Buticaps
Butisol Sodium (Butobarbital)
Luminal (Phenobarbital)
Mebaral (Mephobarbital)
Mephyltaletten
Nembutal
Nembutal Sodium (Phenobarbital)
Oramon (Aprobarbital or aprobarbitone),
Pentothal (Thiopental sodium)
Phemiton
Prominal (Methylophenobarbital)
Sarisol
Seconal (Secobarbital)
Somnifaine (Aprobarbital or aprobarbitone),
Surital (Thiamylal)
Generic Names:
Amobarbital sodium
Aprobarbital
Butabarbital
Mephobarbital (methylophenobarbital)
Methohexital
Pentobarbital
Phenobarbital
Primidone (desoxyphenobarbital)
Secobarbital
Thiopental sodium
Thyamilal
Ultra Short-Acting:
Brevital (Methohexital)
Pentothal (Thiopental sodium)
Surital (Thiamylal)
Short-Acting to Intermediate Acting:
Amytal (Amobarbital)
Alurate (Aprobarbital)
Butisol (Butobarbital)
Nembutal (Phenobarbital)
Seconal (Secobarbital)
Long-Acting:
Luminal (Phenobarbital)
Mebaral (Mephobarbital)
Prominal (Methylophenobarbital)
Combination Barbiturates:

Combinations of Butalbital (barbiturate) and Acetaminophen (pain reliever) are available in the following brand names:
Anolor 300
Bupap
Capacet
Cephadyn
Dolgic LQ
Esgic
Esgic-Plus
Ezol
Fioricet
Geone
Margesic
Orbivan CF
Phrenilin
Phrenilin Forte
Zebutal Ketamine anesthesia following administration of a barbiturate for preoperative anxiety and sedation has been reported to produce profound respiratory depression. ("Barbiturates," in The Pharmacological Basis of Therapeutics. 8th ed. New York, N.Y. Pergamon Press, 1990., p. 1320, Gilman, A. G., T. W. Rall, A. S. Nies and P. Taylor (eds.)).

Barbiturates and benzodiazepines can be used to treat seizures and/or status epilepticus. Phenobarbital and other barbiturates enhance inhibitory neurotransmission by binding to a specific barbiturate site on the GABAA receptor. Intravenous phenobarbital is used in the treatment of refractory status epilepticus. Dosing can range from 10 to 20 mg/kg. The use of such high doses of phenobarbital can cause respiratory depression and depression of central cardiovascular function, which can contribute to a "shock-like" condition requiring medical support. One advantages of phenobarbital is a relatively rapid infusion time and efficacy. The main drawbacks of phenobarbital are sedation, respiratory depression, and hypotension.

Benzodiazepines

Benzodiazepines are man-made medications that cause mild to severe depression of the nerves within the brain (central nervous system) and sedation (drowsiness), and have largely replaced barbiturates for treatment of anxiety, nervousness, muscle spasms, seizures, sleeplessness, alcohol withdrawal, status epilepticus, premenstrual syndrome, and panic and sleep disorders. Benzodiazepines are also used as sedatives during surgery.

Seizures, anxiety, and other diseases that require benzodiazepine treatment may be caused by excessive activity of nerves in the brain. These drugs may work by enhancing the effects of gamma-aminobutyric acid (GABA) in the brain. Gamma-aminobutyric acid is a neurotransmitter, a chemical that nerves in the brain use to send messages to one another. Gamma-aminobutyric acid reduces the activity of nerves in the brain and increasing the effect of GABA with a benzodiazepine, reduces brain activity. One serious side effect of benzodiazepines is respiratory depression.

Acute toxicity and/or overdose of carbamazepine can effect respiration, causing irregular breathing and/or respiratory depression. A few cases of neonatal seizures and/or respiratory depression associated with maternal Tegretol and other concomitant anticonvulsant drug use have been observed. A few cases of neonatal vomiting, diarrhea, and/or decreased feeding have also been reported in association with maternal Tegretol use. These symptoms may represent a neonatal withdrawal syndrome.

Similarly, diazepam or barbiturates may aggravate respiratory depression (especially in children), hypotension, and coma. However, barbiturates should not be used if drugs that inhibit monoamine oxidase have also been taken by the patient either in overdosage or in recent therapy (within 1 week).

Examples of Oral Benzodiazepines are:
alprazolam (Xanax, Xanax XR)
clobazam (Onfi)
clonazepam (Klonopin)
clorazepate (Tranxene)
chlordiazepoxide (Librium)
diazepam (Valium, Diastat, Acudial, Diazepam Intensol)
estazolam (Prosom is a discontinued brand in the US)
lorazepam (Ativan)
oxazepam (Zaxopam, Serax is a discontinued brand in the US)
temazepam (Restoril)
triazolam (Halcion)

Formulations of Benzodiazepines

All oral benzodiazepines are available in tablet forms.
Alprazolam and clorazepate are available as extended-release tablets.
Alprazolam, clobazam, diazepam, and lorazepam are available in oral liquid form.
Alprazolam and clonazepam are available in orally dissolving tablets.
Chlordiazepoxide, oxazepam, and temazepam are available in capsule form.
Diazepam also is available as a rectal gel (Diastat).
Some benzodiazepines are available for injection.

Epilepsy is associated with a two to three-fold increase in premature mortality compared to the general population. A major cause for this premature mortality increase is Sudden Unexpected Death in Epilepsy (SUDEP), which occurs under benign circumstances associated with terminal seizures but excludes injury, drowning, trauma, toxicological effect, or status epilepticus-related deaths. Most of the witnessed clinical cases of SUDEP reported generalized seizures leading to respiratory and cardiac failure. The lifetime risk of SUDEP among epileptics is estimated to be up to 8%, and young persons with epilepsy are at a 24 or 28-fold higher risk of sudden unexpected death than the general population. SUDEP ranks second only to stroke among neurologic diseases, in terms of potential years of life lost. The major pathophysiological mechanisms that have been implicated in SUDEP include respiratory failure, cardiac arrhythmia and cerebral shutdown. Because no effective treatments are currently available, there is a pressing need to find drugs that could prevent SUDEP. One measure of severity of seizures is to count the frequency and/or duration.

Although estimates vary, some studies suggest that each year there are about 1.16 cases of SUDEP for every 1,000 people with epilepsy. Most, but not all, cases of SUDEP occur during or immediately after a seizure, and although the exact cause is not known, but the following is a list of factors that may play a role:

Breathing.

A seizure may cause a person to have pauses in breathing due to apnea, or to airway obstruction. If these pauses last too long, they can reduce the oxygen in the blood to a life-threatening level. Heart rhythm. A seizure may cause a dangerous heart rhythm or even heart failure. Other causes and mixed causes. SUDEP may result from more than one cause or a combination involving both breathing difficulty and abnormal heart rhythm.

Three drugs that are especially effective for partial onset seizures are vigabatrin, a selective and irreversible GABAtransaminase inhibitor that greatly increases whole-brain levels of GABA; tiagabine, a potent inhibitor of GABA uptake into neurons and glial cells; and topiramate, which is believed to produce its antiepileptic effect through several mechanisms, including modification of Na$^+$-dependent and/or Ca$^{2+}$-dependent action potentials, enhancement of GABA-mediated Cl$^-$ fluxes into neurons, and inhibition of kainate-mediated conductance at glutamate receptors of the AMPA/kainate type. (Angehagen, et al., 2003, *Neurochemical Research*, 28(2):333-340).

Tiagabine (trade name Gabitril) is an anticonvulsant medication used in the treatment of epilepsy. The drug is also used off-label in the treatment of anxiety disorders and panic disorder. Tiagabine overdose can produce neurological symptoms such as lethargy, single or multiple seizures, status epilepticus, coma, confusion, agitation, tremors, dizziness, dystonias/abnormal posturing, and hallucinations, as well as respiratory depression, tachycardia, hypertension, and hypotension. Overdose may be fatal especially if the victim presents with severe respiratory depression and/or unresponsiveness.

The DBA/1 mouse model of SUDEP exhibits a chronic, abnormally high degree of susceptibility to fatal seizures (seizure-induced death) induced by electroconvulsive shock, hyperthermia, convulsant drug, and acoustic stimulation. High intensity acoustic stimuli induce audiogenic seizures (AGSz), which consist of tonic-clonic seizures followed by seizure-induced respiratory arrest (S-IRA) that leads to death in the immediate post-ictal period. Timely mechanical support of respiration can consistently reverse S-IRA in this SUDEP model. (Faingold C L, Randall M, Tupal S. 2010. DBA/1 mice exhibit chronic susceptibility to audiogenic seizures followed by sudden death associated with respiratory arrest. *Epilepsy Behav.* 17:436-40).

Studies have elucidated deficits in serotonin production and receptor expression in DBA/1 mice. Many, but not all drugs that enhance serotonergic neurotransmission, including selective serotonin reuptake inhibitors (SSRIs), such as fluoxetine, fluvoxamine and sertraline, or inhibit serotonin-norepinephrine reuptake, such as venlafaxine and atomoxetine, have been reported to prevent seizure-induced respiratory failure and death in DBA mice in a dose-dependent manner. In contrast, serotonin antagonists enhance the susceptibility of DBA mice to S-IRA. These findings and additional studies on other SUDEP models have led to a serotonergic hypothesis of SUDEP.

The serotonin hypothesis of SUDEP is based on findings that treatments which modify serotonergic function significantly alter susceptibility to seizure-induced sudden death in several epilepsy models, including DBA/1 mice. Serotonergic abnormalities have also recently been observed in human SUDEP.

As disclosed in US Patent Application publication 2018/0092864 (U.S. Ser. No. 15/717,159), the contents of which are incorporated herein by reference in their entirety, methods are provided for determining the binding characteristics, activity (e.g., agonist or antagonist) selectivity, specificity and pharmaceutical effects of fenfluramine and fenfluramine analogs at various receptors, including (5-HT) receptor sub-types, (e.g., 5-HT$_{1A}$, 5-HT$_{1D}$, 5-HT$_{1E}$, 5-HT$_{2A}$, 5-HT$_{2C}$, 5-HT$_4$, 5-HT$_{5A}$ and 5-HT$_7$) as well as other receptors, such as, for example, an adrenergic receptor (e.g., the beta-1 or beta-2 adrenergic receptors), a muscarinic acetylcholine receptor protein (e.g., the M1, M2, M3, M4 or M5 muscarinic acetylcholine receptor), a chaperone protein (e.g., the Sigma 1 or Sigma-2 receptors), or a voltage-gated sodium channel subunit protein or a subunit thereof (e.g., the Nav 1.1, Nav 1.2, Nav 1.3, Nav 1.4, Nav 1.5, Nav 1.6, or Nav 1.7) and/or a neurotransmitter transport protein (e.g., a serotonin transporter (SET), a dopamine transporter (DAT), and a norepinephrine transporter (NET)). Testing in animal models led to the unexpected discovery that certain of those candidates surprisingly reduced epileptiform activity in in vivo animal models.

Recently, the contributions of several serotonin receptor subtype(s) in mediating the action of fenfluramine in blocking seizure-induced sudden death were evaluated in the DBA/1 mouse model of SUDEP. In these studies, fenfluramine, known to enhance the release of serotonin (5-hydroxytryptamine, 5-HT) in the brain, was discovered to be effective in blocking audiogenic seizures (AGSz) and seizure-induced respiratory arrest (S-IRA) in DBA/1 mice.

The present disclosure is directed to the surprising discovery that certain serotonin receptors (also known as 5-hydroxytryptamine (5-HT) receptors) mediate the action of fenfluramine (FFA) in blocking seizure-induced sudden death and seizure-induced respiratory arrest (S-IRA) in mice. Specifically, the present disclosure is directed to the surprising discovery that fenfluramine is useful in treating, reducing and/or ameliorating the risk or occurrence of respiratory depression and/or seizure-induced respiratory arrest (S-IRA) associated with use of one or more opioids, barbiturates and/or benzodiazepines in a human patient.

Without being bound by theory, fenfluramine (FFA) enhances serotonergic neurotransmission by augmenting carrier-mediated synaptic release of serotonin (5-HT) in the brain due to disruption of its vesicular storage and inhibiting its reuptake. Its active metabolite, norfenfluramine (N-FFA), contributes to prolonging this effect. Recent clinical studies found treatment with FFA to be effective as an add-on (adjunctive) agent to improve seizure control in patients with the intractable seizures characteristic of Dravet syndrome, which is difficult to treat and has a tragically high risk of SUDEP. Seizure activity was significantly reduced in frequency and/or severity, and in some cases eliminated entirely, by administering the drug fenfluramine.

The present disclosure is the first study to investigate the efficacy of FFA on respiratory depression due to opioids, barbiturates and/or benzodiazepines in a mammalian mouse model. Thus, the present disclosure is directed to elucidating the effects of FFA on respiratory depression. The effect of FFA on seizure-induced respiratory arrest (S-IRA) in DBA/1 mice was investigated.

As described herein, several 5-HT receptor-specific antagonists were used to investigate fenfluramine's effects, to determine whether the 5-HT antagonists could reverse the anticonvulsant activity (and/or S-IRA blocking, or any other effect) mediated by fenfluramine, thereby allowing identification of a subset of 5-HT receptors to which fenfluramine binds and acts as an agonist.

For these experiments, after subjecting DBA/1 mice to the established priming procedure to assure consistent susceptibility to S-IRA following AGSz, the mice were used to assess the effects of fenfluramine on various 5-HT receptor subtypes. Seizures were induced using an electrical bell, and resuscitation was accomplished using a rodent respirator (Faingold et al., 2010). At least 24 hours after priming, the mice received FFA (15 mg/kg, i.p.) and were tested for AGSz and S-IRA susceptibility 16 hours later. Thirty minutes prior to AGSz induction, a selective 5-HT receptor antagonist or vehicle was administered to evaluate if a specific receptor contributes to the ability of FFA to block S-IRA. Seizure behaviors were recorded on videotape, quantified, and compared statistically with vehicle-treated negative and FFA-treated positive controls (Chi-Square Test; significance set at p<0.05).

Specifically, the antagonists tested were: the 5-HT$_{1A}$ antagonist WAY100635 (0.1-15 mg/kg); the 5-HT$_2$ antagonist Ritanserin (10-20 mg/kg); the 5-HT$_3$ antagonist Ondansetron (1-3 mg/kg); the 5-HT$_4$ antagonist GR125487 (20-60 mg/kg); the 5-HT$_{5A}$ antagonist SB669551 (10-20 mg/kg); and the 5-HT$_7$ antagonist SB269970 (30-40 mg/kg). Studies investigating the effect of 5-HT$_6$ and 5-HT$_{1a/1b}$ antagonists are also underway.

Notably, a reversal of the FFA-induced reduction in the incidence (frequency) of S-IRA was observed following treatment with the 5-HT$_4$ antagonist (GR125487, 30 mg/kg). This dose was effective in inducing a significant (p<0.05) blockade of this of the FFA-induced reduction in S-IRA. While the antagonists of 5-HT$_2$, 5-HT$_4$ and 5-HT$_7$ receptors were found to reverse the anticonvulsant effect of FFA against the severity of AGSz in the mice, but not FFA's S-IRA blocking effect, 5-HT$_{1a}$ and 5-HT$_3$ receptor antagonists were not effective at any dose tested.

Specifically, a significant (p<0.05) partial reversal of the FFA-induced S-IRA blockade was observed following 30-minutes treatment with the 5-HT$_4$ antagonist (GR125487, 30 mg/kg). Thus, GR125487 was effective in inducing a significant blockade of fenfluramine's inhibition of S-IRA. Interestingly, antagonists of 5-HT$_2$, 5-HT$_4$ and 5-HT$_7$ receptors were found to reverse the anticonvulsant effect of FFA against the severity of AGSz but not its S-IRA blocking effect.

The antagonists of 5-HT$_2$ (20 mg/kg Ritanserin), 5-HT$_4$ (30 and 60 mg/kg GR125487) and 5-HT$_7$ (30 mg/kg and 40 mg/kg SB269970) receptors were able to reverse FFA's anticonvulsant effect against the severity of AGSz. The 5-HT$_{5a}$ antagonist SB669551 blocked FFA's anticonvulsant effect at 20 mg/kg. In contrast, 5-HT$_{1A}$ (WAY100635 at 0.1-15 mg/kg) and 5-HT$_3$ (Ondansetron at 1-3 mg/kg) receptor antagonists were not effective at any dose tested.

These findings suggest that the anticonvulsant effect of FFA against S-IRA induced by AGSz in DBA/1 mice is mediated, relatively selectively, as a result of activation of 5-HT$_4$ receptors. It may be relevant that the expression levels of 5-HT$_4$ receptors in the DBA/1 mouse brain is not significantly different from that in normal mice (Faingold et al., 2011). The results were surprising in light of previous studies on the receptors that mediate the ability of a selective serotonin re-uptake inhibitor to reduce seizure severity and block S-IRA can be reversed only by a selective 5-HT$_3$ antagonist (Faingold et al., 2016). Thus, agonists which activate specific 5-HT receptors (e.g., 5-HT$_4$ receptor agonists) are of interest for future studies in animal models of SUDEP and as a potential preventative treatment for human SUDEP.

Generally, antagonists of the 5-HR$_{1A}$, 5-HT$_3$, and receptors did not reverse fenfluramine's effect, suggesting that fenfluramine's effect on S-IRA and/or AGSz is not mediated by an interaction with these receptors. In contrast, the 5-HT$_2$, 5-HT$_{5A}$, 5-HT$_7$ antagonists (Ritanserin at 20 mg/kg; SB669551 at 20 mg/kg; and SB269970 at 30 mg/kg and 40 mg/kg) were found to block FFA's anticonvulsant effect, suggesting that fenfluramine's anticonvulsant effect may be mediated by its interaction of these receptors.

Notably, because the compound GR125487 was found to partially reverse fenfluramine's anticonvulsant effects and S-IRA blocking effects, it was concluded that fenfluramine was found to act specifically as an agonist at the 5-HT$_4$ receptor.

Thus, the anticonvulsant effect of FFA against S-IRA induced by AGSz in DBA/1 mice is mediated, at least in part, by activation of 5-HT$_4$ receptors. The expression level of 5-HT$_4$ receptors in the DBA/1 mouse brain is not significantly different from that in normal mice (Faingold et al., 2011). These results were surprising in light of previous studies on the receptors that mediate the ability of a selective serotonin re-uptake inhibitor to reduce seizure severity and block S-IRA can be reversed only by a selective 5-HT$_3$ antagonist (Faingold et al., 2016).

Agonists which activate specific 5-HT receptors are of interest for future studies in animal models of SUDEP and as a potential preventative treatment for human SUDEP.

Known 5-HT receptors include: 5-HT$_1$, 5-HT$_{1A}$, 5-HT$_{1B}$, 5-HT$_{1C}$, 5-HT$_{1D}$, 5-HT$_{1E}$, 5-HT$_{1F}$, 5-HT$_2$, 5-HT$_{2A}$, 5-HT$_{2B}$, 5-HT$_{2C}$, 5-HT$_3$, 5-HT$_4$, 5-HT$_5$, 5-HT$_{5A}$, 5-HT$_{5B}$ 5-HT$_6$, and 5-HT$_7$ amongst others. In some embodiments of the present disclosure, the 5-HT receptor is 5-HT$_4$. In some embodiments of the present disclosure, the 5-HT receptor agonist is a 5-HT$_4$ receptor agonist. In some embodiments of the present disclosure, the 5-HT$_4$ receptor agonist is fenfluramine. In certain embodiments of this disclosure, the patient has been diagnosed with epilepsy. In certain embodiments of this disclosure, the patient has respiratory depression due to the use of an opioid, barbiturate and/or benzodiazepine.

FFA has a specific effect at a particular 5-HT receptor subtype, and 5-HT receptor-specific antagonists could reverse the anticonvulsant effects and S-IRA blocking effects of FFA. Fenfluramine (FFA), was found to enhance the release of serotonin (5-hydroxytryptamine, 5-HT) in the brain, was found to be effective in blocking audiogenic seizures (AGSz) and seizure-induced respiratory arrest in these DBA/1 mice.

In some embodiments of this disclosure, the 5-HT receptor is 5-HT$_4$. As disclosed herein, fenfluramine was found to act as an anticonvulsant at 5-HT$_4$ receptors to prevent seizure-induced respiratory arrest (S-IRA) and seizure-induced Sudden Unexpected Death in Epilepsy (SUDEP) in the DBA/1 mouse model. Furthermore, the present study identifies fenfluramine as a 5-HT$_4$ receptor agonist able to reverse respiratory depression in a subject using one or more opioids, barbiturates, and/or benzodiazepines.

Fluoxetine, a 5-HT re-uptake inhibitor (SSRI), can prevent S-IRA in DBA/1 mice by acting via 5-HT$_3$ receptors (Faingold, et al., 2011, Epilepsy Behav. 22:186-190; Faingold, et al., 2016, Epilepsy Behav. 64(Pt A):166-170). Fenfluramine (FFA), which enhances 5-HT release in the brain, is an effective add-on in Dravet syndrome patients (Ceulemans, et al., 2016, Epilepsia 57:e129-34; Schoonjans, et al., 2017, Eur J Neurol. 24(2):309-314) and is able to block AGSz and S-IRA in DBA/1 mice. The 5-HT$_{1-7}$ receptors, known to be expressed in brainstem cardiorespiratory networks, are implicated in modulating respiration (Hilaire et al., 2010, Respir. Physiol. Neurobiol. 174(1-2):76-88). Therefore, in order determine the mechanism of action of FFA, the role of the 5-HT receptors in mediating anticonvulsant and S-IRA prophylaxis effect of FFA in DBA/1 mice was investigated.

Specific Aspects of the Invention

Provided are therapeutic agents that are useful in preventing, treating, or ameliorating symptoms associated with a disease or disorder in a patient diagnosed with the disease or disorder, including but not limited to patients diagnosed with respiratory depression or seizure-induced respiratory arrest (S-IRA) which can lead to Sudden Unexpected Death in pilepsy (SUDEP), and pharmaceutical compositions and formulations comprising those agents that are useful in practicing the methods of the invention.

Therapeutic Agents

The inventors have made the surprising discovery that certain therapeutic agents (e.g. fenfluramine (FFA)) are useful in treating diseases or disorders, including but not limited to respiratory depression or seizure-induced respiratory arrest (S-IRA). Thus, in accordance with one aspect of the present disclosure, provided herein are therapeutic agents useful in treating patients diagnosed with a disease or disorder and/or in preventing or ameliorating symptoms of those diseases or disorders exhibited by the patient.

Dosage/Frequency of Administration: Dosage forms can be formulated for once a day administration, or for multiple daily administrations (e.g. 2, 3 or 4 times a day administration). Alternatively, for convenience, dosage forms can be formulated for less frequent administration (e.g., monthly, bi-weekly, weekly, every fourth day, every third day, or every second day), and formulations which facilitate extended release are known in the art.

As used herein, the phrase "semi-chronic administration" refers to administration of a therapeutic agent, such as fenfluramine or a $5-HT_4$ receptor agonist, for a period of several days, a week, several weeks, a month, several months, a year, or several years.

Binding of Single or Multiple Targets

In some embodiments, the therapeutic agents provided by the disclosure can bind one or more targets, for example, two or more targets, three or more targets, four or more targets, five or more targets, or more.

Receptor Protein Targets

In some embodiments, the therapeutic agent binds a $5-HT_4$ receptor.

In some embodiments, the therapeutic agent binds to the sigma-1 receptor and one or more 5-HT receptors, for example, the $5-HT_{1A}$ receptor, the $5-HT_{1D}$ receptor, the $5-HT_{1E}$ receptor, the $5-HT_{2A}$ receptor, the $5-HT_{2C}$ receptor, the $5-HT_4$ receptor, the $5-HT_{5A}$ receptor, and/or the $5-HT_7$ receptor. In some embodiments, the therapeutic agent binds to the sigma-1 receptor and the $5-HT_4$ receptor.

Functional Activity

In accordance with the present disclosure, the terms "active" or "activity" are used herein to mean having an effect on cell, nuclear, or tissue function, and is intended to encompass agonist activity, inverse agonist activity, antagonist activity, synergy, allosteric agonism, allosteric modulation, including positive, negative and neutral allosteric modulation, ago-allosteric modulation, including positive, negative, and neutral ago-allosteric modulation, and ligand trapping.

Receptor Activity

In some embodiments, the therapeutic agent is active at one or more 5-HT receptor proteins selected from the group consisting of the $5-HT_{1A}$ receptor, the $5-HT_{1D}$ receptor, the $5-HT_{1E}$ receptor, the $5-HT_{2A}$ receptor, the $5-HT_{2C}$ receptor, the $5-HT_4$ receptor, the $5-HT_{5A}$ receptor, and/or the $5-HT_7$ receptor. In some embodiments, the therapeutic agent activates the $5-HT_4$ receptor.

Therapeutic Agents Active at Multiple Targets

The disclosure further provides therapeutic agents that are active one or more targets, for example, two or more targets, three or more targets, four or more targets, five or more targets, or more.

For example, in one embodiment, the disclosure provides therapeutic agents that are active at two or more 5-HT receptors. In this regard, the present disclosure is directed to the surprising discovery that fenfluramine acts on the $5-HT_4$ receptors and is useful in preventing, treating or ameliorating symptoms such as seizure-induced respiratory arrest (S-IRA) leading to Sudden Unexpected Death in Epilepsy (SUDEP) in patients having a seizure disease or disorder, epilepsy and/or epileptic encephalopathy.

Therapeutic Agents which are Inactive at the $5-HT_{2B}$ Receptor

In preferred embodiments, the therapeutic agents disclosed herein are not active at the $5-HT_{2B}$ receptor to an extent sufficient to cause adverse effects such as valvulopathy, pulmonary hypertension or other adverse effects. In alternate exemplary embodiments, the agents do not bind the $5-HT_{2B}$ receptor, or are $5-HT_{2B}$ antagonists (i.e., agents that block the activity of agonists), or are $5-HT_{2B}$ inverse antagonists (i.e., agents that decrease basal activity of the receptor), or are neutral agonists (i.e., compounds that block binding of agonists) of the $5-HT_{2B}$ receptor.

Diseases and Disorders

The therapeutic agents provided by the disclosure are useful in treating a number of diseases and disorders, and/or in reducing or ameliorating their symptoms. For example, the therapeutic agents disclosed herein are useful for treating respiratory depression or seizure-induced respiratory arrest (S-IRA), and in preventing, reducing or ameliorating their symptoms in patients diagnosed with those conditions.

Methods of Use

The above-described therapeutic agents can be employed in a variety of methods. As summarized above, aspects of the method include administering a therapeutically effective amount of a therapeutic agent as described herein to treat a patient in need of treatment, for example, to a patient diagnosed with a disease or condition of interest, or to prevent, reduce or ameliorate symptoms of a disease or disorder in patients diagnosed with that disease or disorder. Examples include seizures, particularly status epilepticus, seizure-induced respiratory arrest (S-IRA), and Sudden Unexpected Death in Epilepsy (SUDEP). By "therapeutically effective amount" is meant the concentration of a compound that is sufficient to elicit the desired biological effect (e.g., treatment or prevention of epilepsy and associated symptoms and co-morbidities, including but not limited to seizure-induced sudden respiratory arrest (S-IRA). Diseases and conditions of interest include, but are not limited to, respiratory depression or seizure-induced respiratory arrest (S-IRA). Also of interest is the prevention or amelioration of symptoms and co-morbidities associated with those diseases In some embodiments, the subject method will be protective of symptoms, including but not limited to respiratory depression, S-IRA, SUDEP, and co-morbid conditions.

Genetic Testing

In some cases, it can be desirable to test the patients for a genetic mutation prior to administration of some of the therapeutic agents provided by the disclosure, especially in cases where use of specific agent is contraindicated either because the agent is ineffective or because it would have undesired or serious side effects. Thus, it is in some cases desirable to test patients prior to treatment. For example, a subject/patient can be tested for the presence of opioids, barbiturates, and/or benzodiazepines, and/or for respiratory depression or seizure-induced respiratory arrest (S-IRA) associated with the use of these drugs.

Other genetic tests can be carried out, and can be required as a condition of treatment.

Dosing

The different therapeutic agents disclosed herein can be dosed to patients in different amounts depending on different patient age, size, sex, condition as well as the use of different therapeutic agents.

For example, the dosing can be a daily dosing based on weight. However, for convenience the dosing amounts can be preset. In general, the smallest dose which is effective should be used for the particular patient. The patient can be dosed on a daily basis using a single dosage unit which single dosage unit can be comprised of the therapeutic agent in an amount appropriate for the particular agent. The dosage unit can be selected based on the delivery route, e.g. the dosage unit can be specific for oral delivery, transdermal delivery, rectal delivery, vaginal delivery, buccal delivery, intranasal and/or inhaled delivery, pulmonary delivery or delivery by injection.

Formulation

The dose of therapeutic agent administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

Particular formulations of the invention are in a liquid form. The liquid can be a solution or suspension and can be an oral solution or syrup which is included in a bottle with a pipette which is graduated in terms of milligram amounts which will be obtained in a given volume of solution. The liquid solution makes it possible to adjust the solution for small children which can be administered in increments appropriate to the particular therapeutic agent.

Administration of the subject compounds can be systemic or local. In certain embodiments, administration to a mammal will result in systemic release of a subject compound (for example, into the bloodstream). Methods of administration can include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, the subject compounds and compositions are administered orally. In certain embodiments, it can be desirable to administer a compound locally to the area in need of treatment. In some embodiments, the method of administration of the subject compound is parenteral administration. This can be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, Combination therapy includes administration of a single pharmaceutical dosage formulation which contains the subject compound and one or more additional agents; as well as administration of the subject compound and one or more additional agent(s) in its own separate pharmaceutical dosage formulation. For example, a subject 5-$HT_4$ receptor agonist (e.g., fenfluramine) and an additional agent—for treating respiratory depression can be administered to the patient together in a single dosage composition such as a combined formulation, or each agent can be administered in a separate dosage formulation. Where separate dosage formulations are used, the subject compound and one or more additional agents can be administered concurrently, or at separately staggered times, e.g., sequentially.

In some embodiments, the subject method is an in vitro method that includes contacting a sample with a subject compound. The protocols that can be employed in these methods are numerous, and include but are not limited to, serotonin release assays from neuronal cells, cell-free assays, binding assays (e.g., 5-$HT_4$ receptor binding assays); cellular assays in which a cellular phenotype is measured, e.g., gene expression assays; and assays that involve a particular animal model for a condition of interest (e.g., respiratory depression or seizure-induced respiratory arrest (S-IRA)) or symptoms or comorbidities associated with such conditions.

Pharmaceutical Preparations

Also provided are pharmaceutical preparations. Pharmaceutical preparations are compositions that include a compound (either alone or in the presence of one or more additional active agents) present in a pharmaceutically acceptable vehicle. The term "pharmaceutically acceptable" means approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal.

The choice of excipient will be determined in part by the particular compound, as well as by the particular method used to administer the composition. Accordingly, there is a wide variety of suitable formulations of the pharmaceutical composition of the present invention.

The dosage form of a therapeutic agent employed in the methods of the present invention can be prepared by combining the therapeutic agent with one or more pharmaceutically acceptable diluents, carriers, adjuvants, and the like in a manner known to those skilled in the art of pharmaceutical formulation.

By way of illustration, the therapeutic agent can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions can contain common carriers and excipients, such as solubilizers, isotonic agents, suspending agents, emulsifying agents, stabilizers, preservatives, colorants, diluents, buffering agents, surfactants, moistening agents, flavoring agents and disintegrators, and including, but not limited to, corn starch, gelatin, lactose, dextrose, sucrose, microcrystalline cellulose, kaolin, mannitol, dicalcium phosphate, sodium chloride, alginic acid, vegetable or other similar oils, synthetic aliphatic acid glycerides, esters of higher aliphatic acids or propylene glycol, corn starch, potato starch, acacia, tragacanth, gelatin, glycerin, sorbitol, ethanol, polyethylene glycol, colloidal silicon dioxide, croscarmellose sodium, talc, magnesium stearate and stearic acid. Disintegrators commonly used in the formulations of this invention include croscarmellose, microcrystalline cellulose, corn starch, sodium starch glycolate and alginic acid. The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

In some cases, the compound is formulated for oral administration. In some cases, for an oral pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition can be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition can also contain minor amounts of non-toxic auxiliary substances such as wetting agents, emulsifying agents, or buffers.

Particular formulations of the invention are in a liquid form. The liquid can be a solution or suspension and can be an oral solution or syrup which is included in a bottle with a pipette which is graduated in terms of milligram amounts which will be obtained in a given volume of solution. The liquid solution makes it possible to adjust the solution for small children which can be administered anywhere from 0.5 mL to 15 mL and any amount between in half milligram increments and thus administered in 0.5, 1.0, 1.5, 2.0 mL, etc.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a powder for reconstitution.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Several selective serotonin (5-HT) reuptake inhibitors were found to prevent seizure-induced respiratory arrest (S-IRA) in DBA mice. However, not all drugs that enhance the activation of 5-HT receptors effectively block S-IRA in DBA mice. Therefore, fenfluramine (FFA) was investigated to determine whether its augmentation of 5-HT release altered susceptibility to audiogenic seizures and S-IRA in DBA/1 mice.

Example 1

Effects of Fenfluramine on Animal Model of SUDEP

Materials and Methods
Animals

These studies involved age matched (<80 days) male DBA/1 mice obtained from ENVIGO. Because there were no significant sex differences in the AGSz incidence (frequency), severity and S-IRA susceptibility in DBA/1 mice, males were used in this study. The mice were primed as described in previous studies (Faingold et al., (2010). *Epilepsy Behav.* 17:436-40; Faingold, et al. (2011) *Brain Res.* 1418:104-10; Faingold, et al., (2011) *Epilepsy Behav.* 22:186-90). Briefly, the mice were maintained on an ad libitum diet under a 12 h light-dark cycle in a temperature and humidity-controlled laboratory animal medicine facility. Starting at postnatal day 23-25, the mice were primed and tested for consistent susceptibility to AGSz and S-IRA by presenting an intense acoustic stimulus, as described previously. The mice exhibiting consistent susceptibility to S-IRA on three consecutive tests were included in the following studies.

Seizure Induction and Resuscitation

AGSz were induced by presenting to each DBA/1 mouse (N=287) an intense (110 dB SPL; re: 0.0002 dynes/cm$^2$) broad-band acoustic stimulus from an electrical bell (Heath Zenith Model #172C-A) installed inside a plastic cylinder (43 cm diameter). using an electrical bell, and resuscitation was accomplished using a rodent respirator (Faingold et al., (2010) DBA/1 mice exhibit chronic susceptibility to audiogenic seizures followed by sudden death associated with respiratory arrest. *Epilepsy Behav.* 17:436-40).

The stimulus was presented until the mouse exhibited tonic seizures or for a maximum duration of 60 s. The typical seizure semiology in the DBA/1 mice begins with a wild running phase, followed by clonic-tonic seizures and then tonic hind-limb extension that immediately leads to S-IRA during post-ictal behavioral depression (PID). The onset of S-IRA was visually determined by the occurrence of respiratory failure following loss of the righting reflex, relaxation of the pinnae, and then a generalized loss of muscle tone. These behaviors are reliable indicators of imminent sudden death in DBA mice. Resuscitation was initiated within 10 s after pinna relaxation and the generalized loss of muscle tone, which was effective in reversing S-IRA and reviving >90% of the mice. The mice were placed in a supine position, and a polyethylene tube (4.4 mm external diameter) connected to the outflow of a rodent respirator (Harvard Apparatus 680), pumping one cc of room air at 200 strokes/min, was the placed over the nostrils, which produced observable displacement of the chest. Respiratory support was provided until spontaneous breathing rhythm returned, which required ~19 sec. The mice were monitored until they regained the righting reflex and then returned to their home cage. Video recordings of seizure behaviors and recovery were made for off-line evaluation and analysis, including the duration of PID, as indicated by time from muscle tone loss to return of the righting reflex.

Behavioral Testing

The experiments herein disclosed examined the dose-response relationship of FFA (10-40 mg/kg, i.p.) on AGSz-induced behaviors in DBA/1 mice compared to vehicle (saline) treated control mice using different seizure-testing protocols. This initial protocol involved induction of AGSz at 30 min, 12 h and 24 h after drug administration, and subsequently at 24 h intervals until susceptibility to S-IRA returned. These studies were aimed at determining whether FFA can reduce the incidence (frequency) and severity of AGSz and susceptibility to S-IRA. Based on these results, the 5-20 mg/kg dose range was selected to determine the time-course of FFA's effect in another group of DBA/1 mice by a second seizure testing protocol using 8 h intervals during the first 24 h to evaluate the time course of effect in greater detail, and subsequently at 24 h periods. To determine the effect of FFA on the severity of AGSz in DBA/1 mice, the ordinal scoring system of De Sarro and coworkers was used: no seizure=0; wild running=1; clonic seizure=2; tonic seizure=3; death/S-IRA=4. The median effective dose ($ED_{50}$) for FFA for blocking AGSz at 30 min following the i.p. injection in DBA/1 mice was calculated using a second order polynomial equation ($y=65.113x^2-2.0715x-63.578$) that gave the best fit ($R^2=0.9989$).

Drugs

Fenfluramine (FFA), kindly provided by Zogenix International, was dissolved in sterile saline vehicle prepared in the laboratory using Sodium Chloride tablets (Catalog number: 07982-100TAB-F) obtained from Sigma-Aldrich (St. Louis, Mo., U.S.A.).

Statistical Analysis

The videos of seizure behaviors were analyzed visually, and the incidence (frequency) of AGSz, seizure severity, and incidence (frequency) of S-IRA following drug treatment were compared statistically to vehicle controls using the Chi-square, Mann-Whitney U or paired samples t-test with SPSS software. The $ED_{50}$ was calculated using SigmaPlot 13 and Microsoft® Excel. The experimental protocols used in these studies were approved by the Laboratory Animal Care and Use Committee of Southern Illinois University School of Medicine, which are in accordance with National Institutes of Health guidelines for the care and use of laboratory animals. Measures to minimize animal usage as well as pain and discomfort were included in these procedures.

DBA/1 male mice (25-26 days) were subjected to AGSz priming involving 3-4 daily seizures by presenting 122 dB SPL (re: 0.0002 dyne/cm$^2$) broadband acoustic stimulus for ≤1 min.

Mice that showed S-IRA were resuscitated by placing the inhalation tube of a rodent respirator (200 strokes/min) over the nose.

At least 24 h after the final priming seizure the consistent S-IRA susceptible mice were given intraperitoneal (i.p.) injection of FFA or vehicle (saline).

The experimental paradigms used to determine the 5-HT receptors that mediate the protective effect of FFA involved:

Determination of dose and time at which FFA-treated mice showed the lowest incidence of S-IRA following tonic seizures: Mice were tested at 8 h intervals after receiving FFA (5-20 mg/kg, i.p.) for 24 h (to determine the selective S-IRA blocking effect). The mice that didn't show a return of S-IRA susceptibility were tested again at 24 h intervals.

Determination of 5-HT receptors that mediate S-IRA prophylaxis and anticonvulsant effect of FFA: Selective 5-HT receptor antagonist were administered (i.p.) 30 min prior to seizure testing.

Behaviors were recorded on videotape and quantified, and changes were analyzed offline using SPSS and Excel software.

The incidence of S-IRA and tonic seizures were analyzed Chi-square test with a significance level set at $p<0.05$.

Dose- and Time-Dependent Effects of FFA on Audiogenic Seizures (AGSz) and S-IRA in DBA/1 Mice.

FFA significantly reduced the incidence of tonic seizures, the AGSz phenotype known to lead to S-IRA, in DBA/1 mice. 10-20 mg/kg of FFA had a blocking effect on S-IRA (FIGS. 1A-1D). The incidence of S-IRA following AGSz in DBA/1 mice was significantly reduced and was long-lasting. Although the tonic AGSz and S-IRA susceptibility returned by approximately 48 h in the mice that received 20 mg/kg FFA, many of these mice continued to show a reduced susceptibility to these seizure behaviors for several days. In contrast, the mice that received 10 mg/kg of FFA showed a shorter-duration of the reduction of S-IRA and tonic seizure at 12 h.

FFA prevented S-IRA in DBA/1 mice. The mice that received 10-20 mg/kg of FFA showed a significant reduction in the incidence of S-IRA starting at 8 h (FIG. 1A). Starting at 8 h following 10, 15 and 20 mg/kg FFA, a significant reduction in the incidence of S-IRA occurred when compared to saline treated controls. The incidence of S-IRA in the mice that received 5 mg/kg FFA was not affected. A return of S-IRA susceptibility among the FFA treated DBA/1 mice occurred at 48 h. [*$p<0.05$; **$p<0.01$; #$p<0.001$ indicate statistically different from controls, respectively, as determined by Chi-square test].

FIG. 1B shows selective S-IRA blocking effect of FFA. A significant reduction in the incidence of S-IRA was seen at the 8 h time point in 100% of the mice following 10-20 mg/kg FFA, and continued to exhibit tonic seizures displayed a significant [#$p<0.001$, Chi-square test] incidence of selective blockade of S-IRA (FIG. 1B). A return of susceptibility to S-IRA in these FFA-treated mice was seen by 48 h.

Figure 1C:
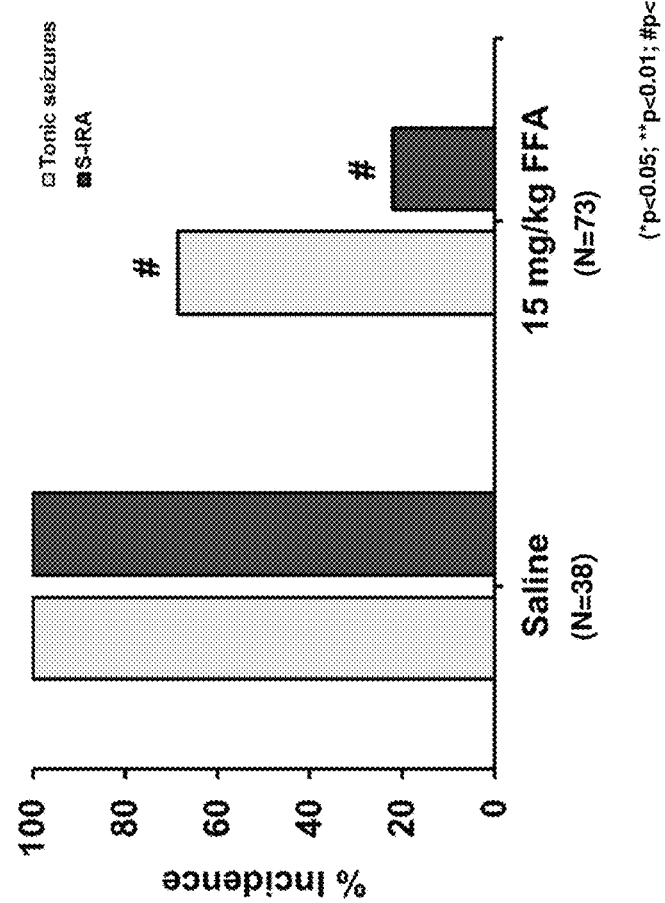
Figure 2B:
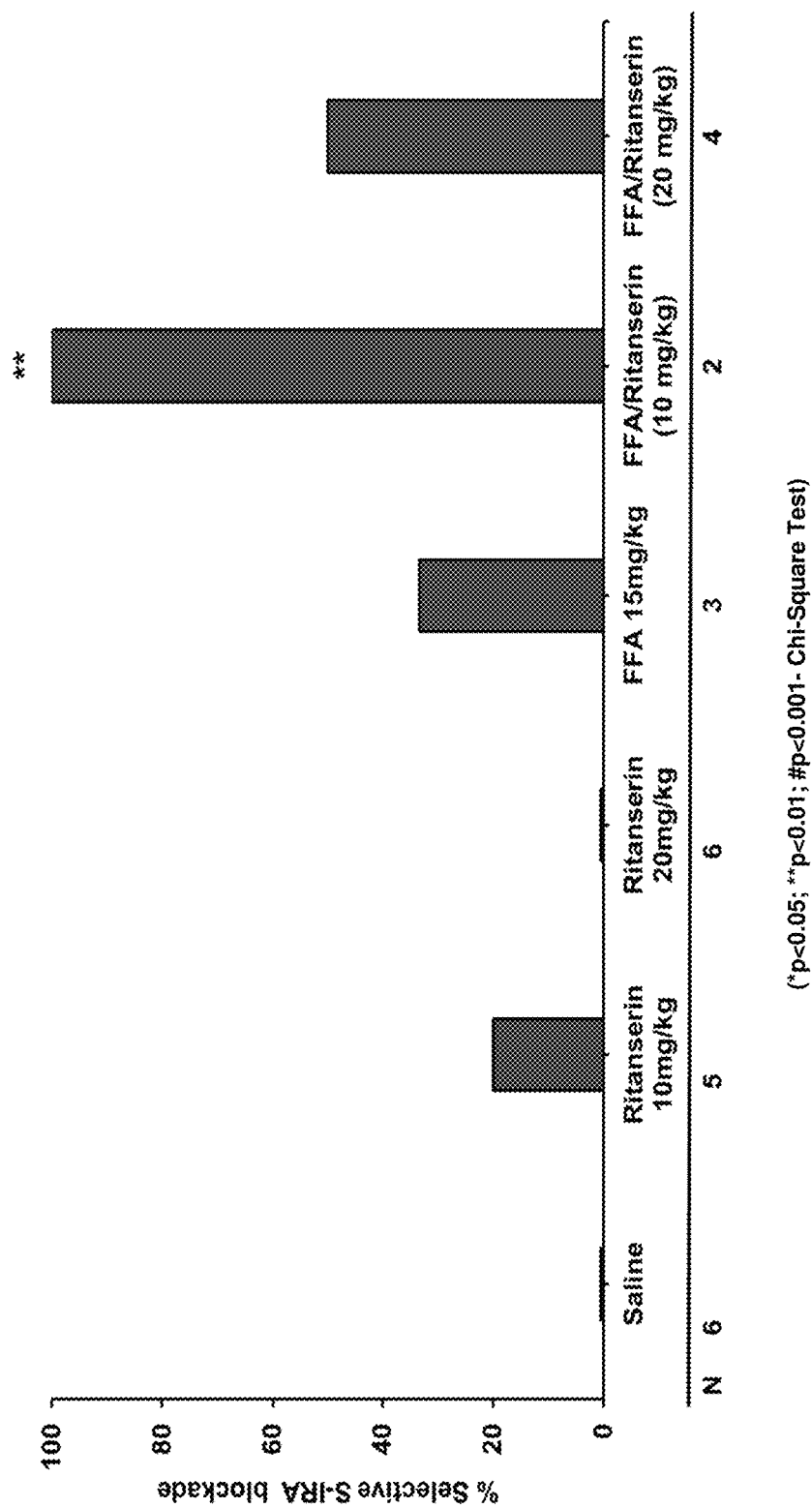
Figure 5A:
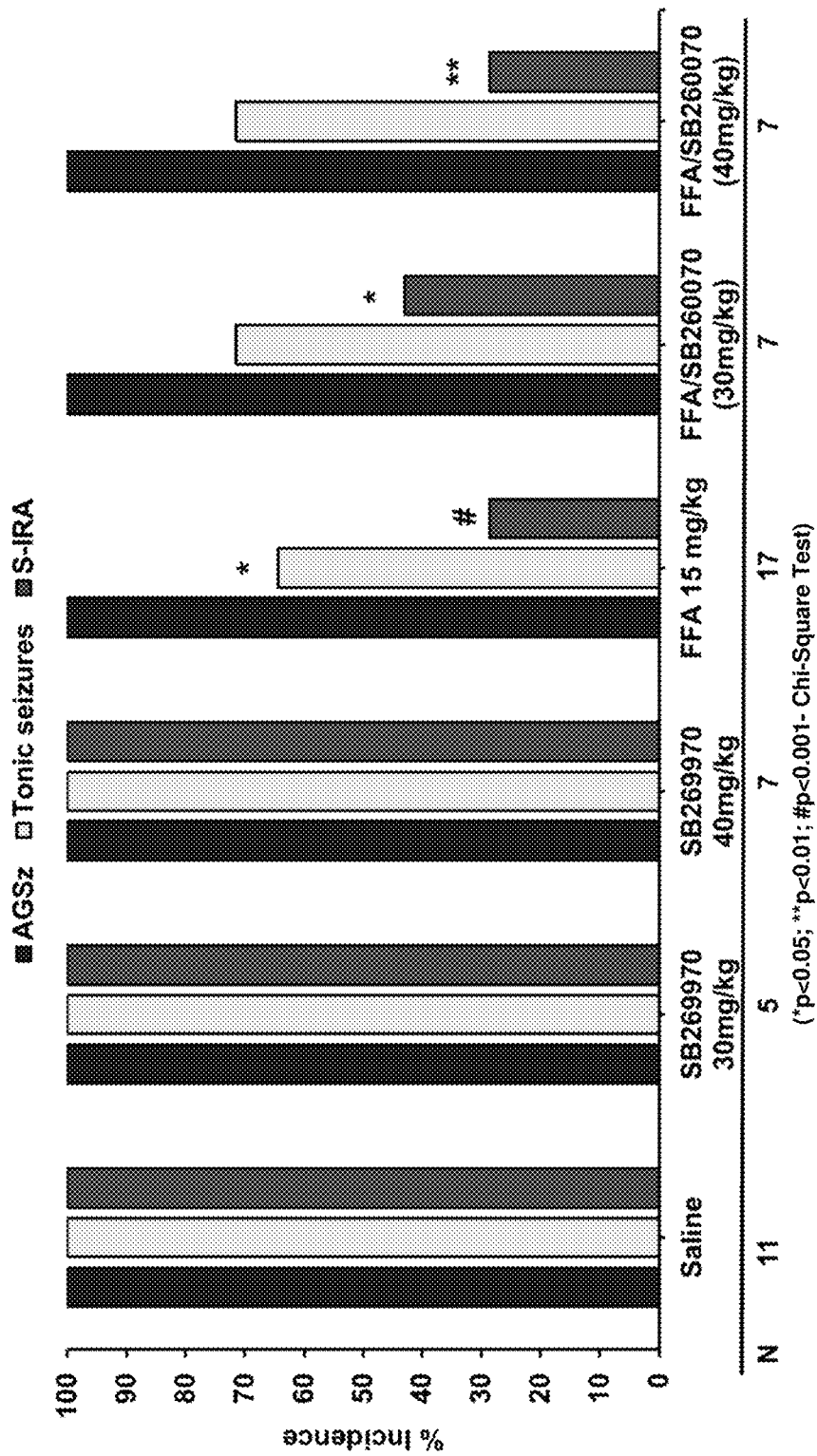
FIGS. 5A-5B: demonstrate that a 5-HT$_7$ receptor antagonist (SB269970) reversed the anticonvulsant effects of FFA in DBA/1 mice.
Figure 5B:
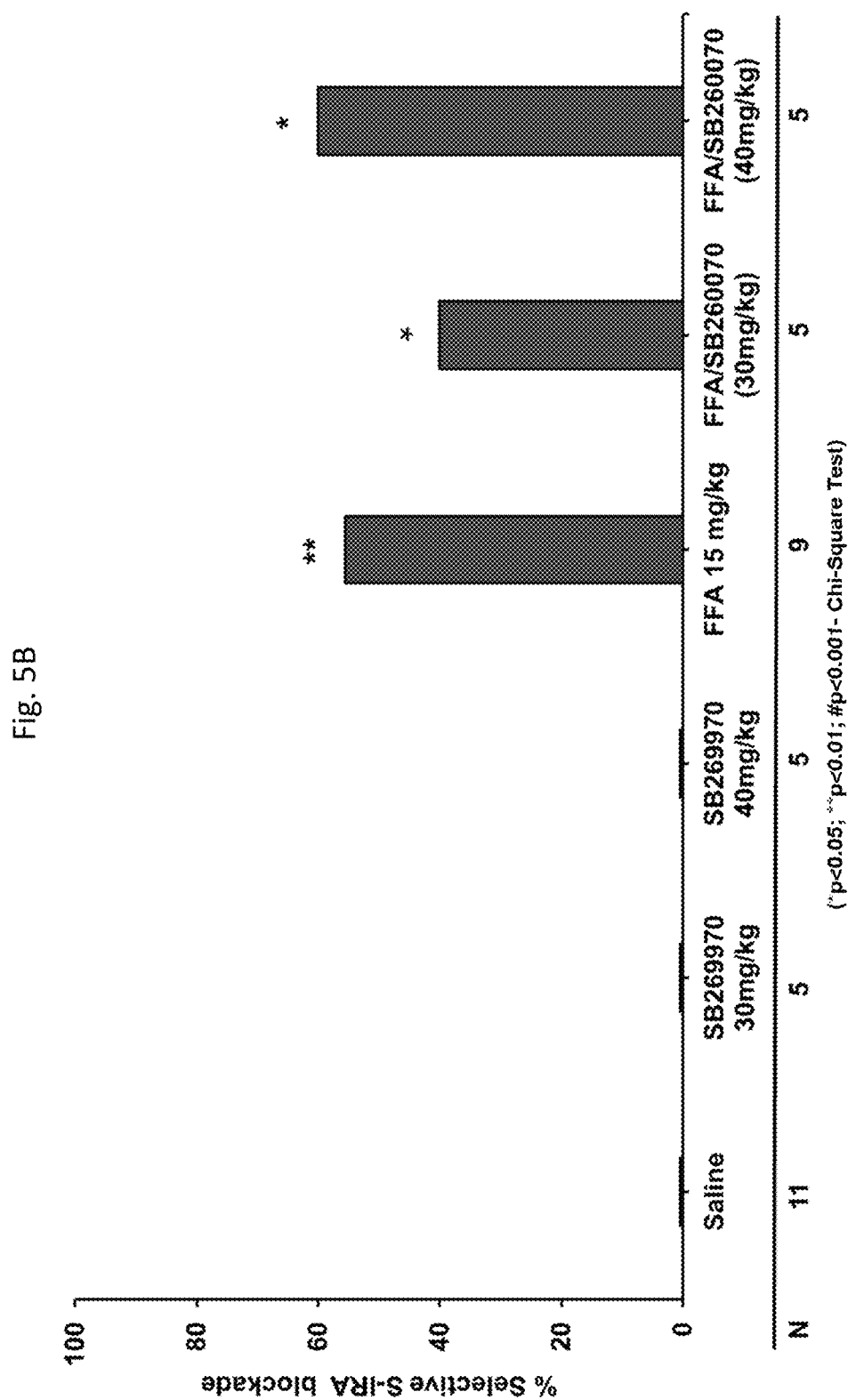

FIGS. 1C-1D show reduction in the incidence of S-IRA and a significant increase in percent selective S-IRA blockade upon treatment with 15 mg/kg FFA (n=73), as compared to saline-treated counterparts (n=38).

To identify a subset of 5-HT receptors to which fenfluramine specifically binds and acts as an agonist, several 5-HT receptor-specific antagonists were evaluated for their ability to reversing fenfluramine's effect on seizure and S-IRA incidence in DBA/1 mice. Antagonists of $5-HT_{1a}$, $5-HT_2$, $5-HT_3$, $5-HT_4$, $5-HT_{5a}$ and $5-HT_7$ receptors were tested and the results are detailed below. Studies investigating the effect of $5-HT_6$ and $5-HT_{1a/1b}$ antagonists are underway.

For these experiments, DBA/1 mice were used (after subjecting to the established priming procedure to assure consistent susceptibility to S-IRA following AGSz) to assess the effects of fenfluramine on various 5-HT receptors. Seizures were induced using an electrical bell, and resuscitation was accomplished using a rodent respirator (Faingold et al., 2010). At least 24 hours after priming, the mice received FFA (10 or 20 mg/kg, i.p.) and were tested for AGSz and S-IRA susceptibility 16 hours later. Thirty minutes prior to AGSz induction, a selective 5-HT receptor antagonist or vehicle was administered to evaluate if a specific receptor contributes to the ability of FFA to block S-IRA. Seizure behaviors were recorded on videotape, quantified, and compared statistically with vehicle-treated negative and FFA-treated positive controls (Chi-Square Test; significance set at $p<0.05$).

Antagonists

Specifically, the antagonists tested were: the $5-HT_2$ antagonist Ritanserin (10-20 mg/kg); the $5-HT_3$ antagonist Ondansetron (2-3 mg/kg); the $5-HT_4$ antagonist GR125487 (20-30 mg/kg); and the $5-HT_7$ antagonist SB269970 (30-40 mg/kg).

Results:

Notably, a partial reversal of the FFA-induced S-IRA blockade was observed following treatment with the $5-HT_4$ antagonist (GR125487, 30 mg/kg). Thus, GR125487 was effective in inducing a significant blockade of fenfluramine's inhibition of S-IRA (See FIGS. 4A and 4B). The antagonists of $5-HT_2$ (10-20 mg/kg Ritanserin), $5-HT_4$ (20 and 30 mg/kg GR125487) and $5-HT_7$ (30 mg/kg and 40 mg/kg SB269970) receptors were able to reverse FFA's anticonvulsant effect against the severity of AGSz. Interestingly, antagonists of $5-HT_2$ and $5-HT_7$ receptors were found to reverse only the anticonvulsant effect of FFA against the severity of AGSz but not its S-IRA blocking effect, suggesting that fenfluramine's anticonvulsant effect may be mediated by its interaction of these receptors. (See FIGS. 2A-2B, and 5A-5B). In contrast, the $5-HT_3$ (Ondansetron at 2-3 mg/kg) receptor antagonist was not effective at any dose tested. Because the compound GR125487 was found to partially reverse fenfluramine's anticonvulsant effects and S-IRA blocking effects, it was concluded that fenfluramine was found to act specifically as an agonist at the $5-HT_4$ receptor.

Thus, the effect of FFA against S-IRA in DBA/1 mice is mediated, at least in part, by activation of $5-HT_4$ receptors. The expression level of $5-HT_4$ receptors in the DBA/1 mouse brain is not significantly different from that in normal mice (Faingold et al., 2011). These results were surprising in light of previous studies on the receptors that mediate the ability of a selective serotonin re-uptake inhibitor to reduce seizure severity and block S-IRA can be reversed only by a selective $5-HT_3$ antagonist (Faingold et al., 2016).

Discussion

Figure 6:
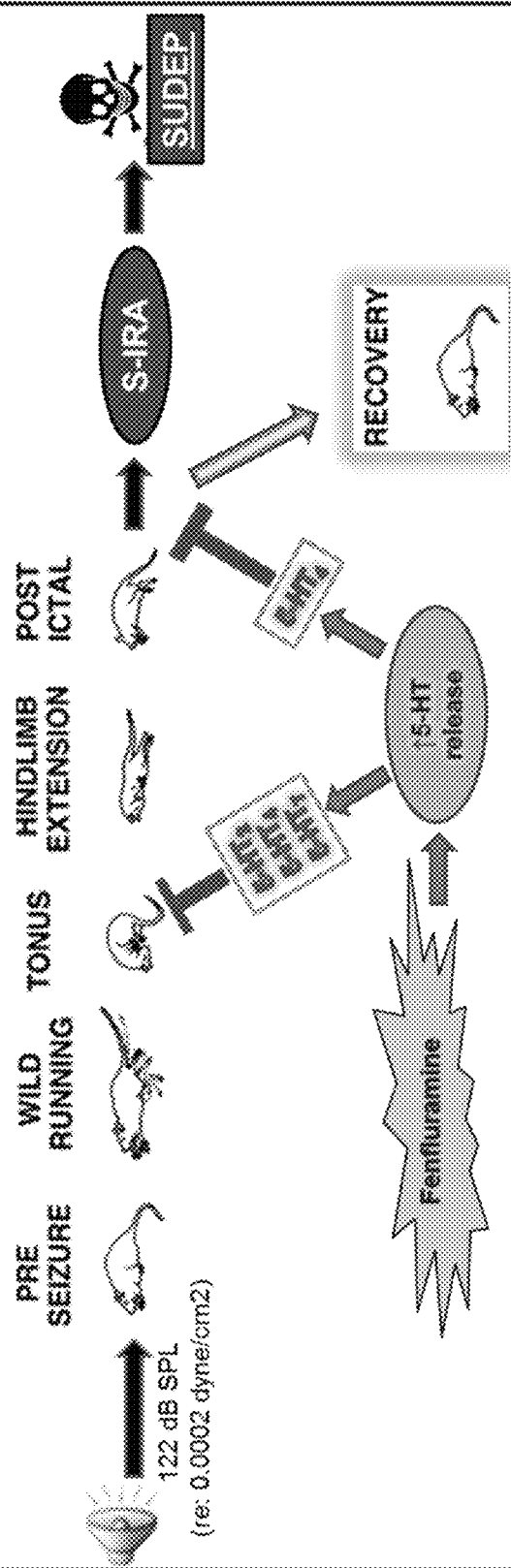
FIG. 6: illustrates the mechanism believed to be involved in the anticonvulsant and S-IRA blocking effects of FFA on various 5-HT receptors in the DBA/1 mouse model.

A model illustrating the presently disclosed discoveries is shown in FIG. 6.

The present study found that FFA administration significantly reduced seizure severity or blocked AGSz susceptibility in DBA/1 mice in a dose- and time-dependent manner. FFA was also found to significantly reduce the incidence of S-IRA, and a selective block of S-IRA without affecting any seizure behavior was also observed. These findings suggest that FFA has the therapeutic potential for improving seizure control and preventing S-IRA and SUDEP.

A significant reversal ($p<0.05$) of the FFA-mediated reduction in S-IRA incidence was induced by the $5-HT_4$ receptor antagonist (GR125487).

The effect of FFA to reduce seizure severity (incidence of tonic seizures) was reversed by the $5-HT_2$ receptor antagonist (ritanserin), $5-HT_4$ receptor antagonist and $5-HT_7$ receptor antagonist (SB269970).

$5-HT_3$ receptors, which are implicated in mediating protective effect of fluoxetine in DBA/1 mice, are not involved in mediating the effect of FFA.

These findings implicate $5-HT_4$ receptors in a crucial role of mediating the S-IRA prophylactic effect of FFA, while the $5-HT_2$ and $5HT_7$ receptors also play a role in modulating the action of FFA in reducing AGSz susceptibility in these mice.

In conclusion, we show for first time that $5-HT_4$ receptors mediate the seizure-induced sudden death prevention effect of FFA in DBA/1 mice.

Studies involving intracerebrovascular injection of $5-HT_4$ and other 5-HT receptor antagonist along with the i.p. injection of FFA are needed to confirm its mechanism of action.

The present study identifies the $5-HT_4$ receptor agonist fenfluramine is useful in mitigating opioid-, barbiturate-and/or benzodiazepine-induced respiratory depression.

Future studies will investigate the protective effect of FFA against opiate-induced respiratory depression, and also the potential prophylactic role of $5-HT_4$ receptor agonists against S-IRA in DBA/1 mice.

Example 3

Further Studies of FFA's Anticonvulsant and S-IRA Blocking Effects

First, because the $5-HT_4$ receptor antagonist (GR125487) was able to significantly reverse the anticonvulsant and S-IRA blocking effects of FFA in the DBA/1 mouse model, further studies will be conducted to investigate the anticonvulsant and S-IRA blocking potential of additional $5-HT_4$ receptor agonists. For example, 10-30 mg/kg BIMU8, alone and in combination with FFA, will be assessed for its effects on AGSz and S-IRA (Manzke et al., 2003; Hasebe et al., 2015).

Additionally, the effect of $5-HT_4$ receptor agonists (e.g., fenfluramine) on reducing ameliorating and/or eliminating seizures, and/or S-IRA and/or SUDEP in a clinical study in humans has been assessed.

Additionally, intracerebrovasular microinjection of GR125487 (10, 20 and 40 nmol) will be performed to further investigate the effects of fenfluramine or other $5-HT_4$ receptor agonists on FFA-like targets in the brain (See De Deurwaerdere et al., 2002; Consolo et al., 1994).

Furthermore, because the $5-HT_4$ receptor antagonist significantly reduced the anticonvulsant and S-IRA suppressant effects of FFA, the role of Sigma 1 receptors in mediating the effect will be investigated. The efficacy of a Sigma 1 receptor antagonist, NE-100, as compared to Sigma 2 antagonist (YUN252), in reversing the effect of FFA on AGSz and the incidence of S-IRA in DBA/1 mice will be studied.

Finally, if Sigma receptor antagonists are able to affect the action of FFA in DBA/1 mice, a follow-up study for the effect of Sigma 1 or 2 agonists and positive allosteric modulator, E1R (10-75 mg/kg), on AGSz and S-IRA in DBA/1 mice will be conducted to further validate this mechanism.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A method of reducing incidence of respiratory depression caused by a toxin in a selected human patient population, comprising:
   selecting a population of human patients exposed to the toxin and thereby at risk of respiratory depression;
   administering to the selected patient population a therapeutically effective dose of a 5-HT4 agonist; and
   allowing the 5-HT$_4$ agonist to stimulate 5-HT$_4$ receptors in the selected patient population, thereby reducing incidence of respiratory depression caused by the toxin in the patient population.

2. The method of any of claim 1 wherein the respiratory depression is intensified by co-ingestion or co-administration of alcohol or other CNS depressants.

3. The method of any of claim 1, wherein the 5-HT$_4$ agonist is selected from the group consisting of fenfluramine, BIMU-8, Cisapride, Mosapride, Prucalopride, Renzapride, RS-67506, Tegaserod, Zacopride, Metoclopramide, and Sulpiride, or a pharmaceutically acceptable salt thereof.

4. The method of claim 1, wherein the 5-HT$_4$ agonist is fenfluramine, or a pharmaceutically acceptable salt thereof; and
   wherein fenfluramine is administered in a therapeutically effective dose as an adjunctive therapeutic agent; and
   wherein the therapeutically effective dose of fenfluramine is selected from the group consisting of 0.2 mg/kg/day to 0.08 mg/kg/day up to a 30 mg maximum daily dose.

5. The method of claim 4, wherein the therapeutically effective dose of fenfluramine is administered in an oral liquid dosage form.

6. The method of claim 1, wherein the 5-HT$_4$ agonist has a characteristic selected from the group consisting of:
   (a) inactive at the 5-HT2B receptor;
   (b) a neutral agonist of the 5-HT2B receptor; and
   (c) an inverse agonist of the 5-HT2B receptor 5-HT2B receptor.

7. The method of claim 6, wherein the patient exhibits a significantly higher responder rate compared with placebo, the method further comprising:
   repeating the administering over a period of days until the patient exhibits a ≥40% reduction from baseline in occurrence of respiratory depression.

8. The method of claim 6, wherein the patient exhibits at least a ≥50% reduction in occurrence of respiratory depression.

9. The method of claim 6, wherein the patient exhibits at least a ≥75% reduction in occurrence of respiratory depression.

10. The method of claim 6, wherein the patient exhibits at least a ≥90% reduction in occurrence of respiratory depression.

11. The method of claim 6, wherein the patient completely free of an occurrence of respiratory depression.

12. The method of claim 1, wherein the 5-HT$_4$ agonist is fenfluramine or a pharmaceutically acceptable salt thereof.

13. The method of claim 2, wherein the 5-HT$_4$ agonist is fenfluramine or a pharmaceutically acceptable salt thereof.

* * * * *